United States Patent
Greenberg et al.

(10) Patent No.: US 10,208,086 B2
(45) Date of Patent: Feb. 19, 2019

(54) CYCLIN A1-TARGETED T-CELL IMMUNOTHERAPY FOR CANCER

(71) Applicant: Fred Hutchinson Cancer Research Center, Seattle, WA (US)

(72) Inventors: Philip Greenberg, Mercer Island, WA (US); Sebastian Ochsenreither, Berlin (DE)

(73) Assignee: Fred Hutchinson Cancer Research Center, Seattle, WA (US)

( * ) Notice: Subject to any disclaimer, the term of this patent is extended or adjusted under 35 U.S.C. 154(b) by 28 days.

(21) Appl. No.: 14/357,512

(22) PCT Filed: Nov. 9, 2012

(86) PCT No.: PCT/US2012/064511
§ 371 (c)(1),
(2) Date: May 9, 2014

(87) PCT Pub. No.: WO2013/071154
PCT Pub. Date: May 16, 2013

(65) Prior Publication Data
US 2014/0322253 A1  Oct. 30, 2014

Related U.S. Application Data

(60) Provisional application No. 61/558,953, filed on Nov. 11, 2011.

(51) Int. Cl.
| | | |
|---|---|---|
| *A61K 38/00* | (2006.01) | |
| *A61K 9/127* | (2006.01) | |
| *C07K 7/08* | (2006.01) | |
| *A61K 39/00* | (2006.01) | |
| *C12N 9/12* | (2006.01) | |
| *C07K 14/47* | (2006.01) | |
| *C07K 7/06* | (2006.01) | |

(52) U.S. Cl.
CPC ............ *C07K 7/08* (2013.01); *A61K 39/0011* (2013.01); *C07K 7/06* (2013.01); *C07K 14/4738* (2013.01); *C12N 9/12* (2013.01); *A61K 38/00* (2013.01); *A61K 2039/5154* (2013.01); *A61K 2039/5158* (2013.01)

(58) Field of Classification Search
CPC .... A61K 2309/5154; A61K 2309/5158; A61K 38/00; A61K 39/0011; C07K 14/4738; C07K 7/06; C07K 7/08; C12N 9/12
USPC .......... 424/185.1, 93.2; 514/21.4, 21.5, 21.6, 514/21.7, 44 R; 530/326, 327, 328, 329
See application file for complete search history.

(56) References Cited

U.S. PATENT DOCUMENTS

| | | |
|---|---|---|
| 6,461,813 B2 | 10/2002 | Lorens |
| 7,342,092 B2 | 3/2008 | Sugiyama |
| 7,608,685 B1 | 10/2009 | Sugiyama et al. |
| 7,622,119 B2 | 11/2009 | Sugiyama |
| 2002/0053092 A1 | 5/2002 | Readhead et al. |
| 2004/0087025 A1 | 5/2004 | June et al. |
| 2010/0047239 A1 | 2/2010 | Wu et al. |
| 2010/0310534 A1 | 12/2010 | Oved et al. |
| 2011/0052530 A1 | 3/2011 | Dudley et al. |
| 2011/0189141 A1 | 8/2011 | Kieback et al. |
| 2011/0236375 A1 | 9/2011 | Lazar et al. |
| 2011/0243972 A1 | 10/2011 | Jaffee |

OTHER PUBLICATIONS

Ochsenreither et al, "Cyclin-A1 represents a new immunogenic targetable antigen expressed in acute myeloid leukemia stem cells with characteristics of a cancer-testis antigen," Blood, Jun. 7, 2012, 119(23): 5492-5501 (printed pp. 1-14).*
Egloff et al, "Cyclin B1 and Other Cyclins as Tumor Antigens in Immunosurveillance and Immunotherapy of Cancer," Cancer Res, 2006, 66(1): 6-9.*
Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.*
Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.*
Rudinger J, "Characteristics of the amino acids as components of a peptide hormone sequence," Peptide Hormones, JA Parsons Edition, University Park Press, Jun. 1976, pp. 1-7.*
"Designing Custom Peptides," from SIGMA Genosys, pp. 1-2. Accessed Dec. 16, 2004.*
Schinzel R, Drueckes P, "The phosphate recognition site of *Escherichia coli* maltodextrin phosphorylase," FEBS, Jul. 1991, 286(1,2): 125-128.*
Berendsen HJC, "A Glimpse of the Holy Grail?" Science, 1998, 282: 642-643.*
Voet D, Voet JG, Biochemistry, Second Edition, John Wiley & Sons, Inc., 1995, pp. 235-241.*
Uebelhoer et al., PLoS Pathogens, 2008, 4: 1-15.*
Ruckwardt et al., J. Immunol. 2010, 185: 4673-4680.*
Kondo et al., J. Immunother., 2009, 32: 157-160.*
Akatsuka et al., "Efficient cloning and expression of HLA class I cDNA in human B-lymphoblastoid cell lines," *Tissue Antigens* 59:502-511, 2002.

(Continued)

*Primary Examiner* — Ileana Popa
(74) *Attorney, Agent, or Firm* — Seed IP Law Group LLP

(57) ABSTRACT

Compositions and methods are provided for eliciting antigen-specific T-cell responses against human cyclin A1 (CCNA1), which is herein identified as a leukemia-associated antigen based on its overexpression in acute myeloid leukemia (AML) including leukemia stem cells (LSC) and in immunologically privileged testis cells, but not in other normal cell types. CCNA1-derived peptide epitopes that are immunogenic for T-cells including CTL are disclosed, as are immunotherapeutic approaches using such peptides for vaccines and generation of adoptive transfer therapeutic cells.

3 Claims, 8 Drawing Sheets

Specification includes a Sequence Listing.

(56) References Cited

OTHER PUBLICATIONS

Blair et al., "Most Acute Myeloid Leukemia Progenitor Cells With Long-Term Proliferative Ability In Vitro and In Vivo Have the Phenotype CD34+/CD71−/HLA-DR−," *Blood* 92(11):4325-4335, 1998.
Bonnet et al., "CD8+ minor histocompatibility antigen-specific cytotoxic T lymphocyte clones eliminate human acute myeloid leukemia stem cells," *Proc. Natl. Acad. Sci. USA* 96:8639-8644, 1999.
Bonnet et al., "Human acute myeloid leukemia is organized as a hierarchy that originates from a primitive hematopoietic cell," *Nature Medicine* 3(7):730-737, 1997.
Brait et al., "Aberrant Promoter Methylation of Multiple Genes during Pathogenesis of Bladder Cancer," *Cancer Epidemiol Biomarkers Prev* 17(10):2786-2794, 2008.
Breems et al., "Prognostic Index for Adult Patients With Acute Myeloid Leukemia in First Relapse," *J Clin Oncol* 23:1969-1978, 2005.
Chaise et al., "DNA vaccination induces WT1-specific T-cell responses with potential clinical relevance," *Blood* 112(7):2956-2964, 2008.
Chan et al., "NGF inhibits human leukemia proliferation by downregulating cyclin A1 expression through promoting acinus/CtBP2 association," *Oncogene* 28:3825-3836, 2009.
Cheever et al., "The Prioritization of Cancer Antigens: A National Cancer Institute Pilot Project for the Acceleration of Translational Research," *Clin Cancer Res* 15(17):5323-5337, 2009.
Cho et al., "Induction of cell apoptosis in non-small cell lung cancer cells by cyclin A1 small interfering RNA," *Cancer Sci* 97(10):1082-1092, 2006.
Coletta et al., "Six1 Overexpression in Mammary Cells Induces Genomic Instability and is Sufficient for Malignant Transformation," *Cancer Res* 68(7):2204-2213, 2008.
Cornelissen et al., "Results of a HOVON/SAKK donor versus no-donor analysis of myeloablative HLA-identical sibling stem cell transplantation in first remission acute myeloid leukemia in young and middle-aged adults: benefits for whom?" *Blood* 109(9):3658:3666, 2007.
Dossett et al, "Adoptive Immunotherapy of Disseminated Leukemia With TCR-transduced, CD8+ T Cells Expressing a Known Endogenous TCR," *Molecular Therapy* 17(4):742-749, 2009.
Doubrovina et al., "In vitro Stimulation with WT1 Peptide-Loaded Epstein-Barr Virus-Positive B Cells Elicits High Frequencies of WT1 Peptide-Specific T Cells with In vitro and In vivo Tumoricidal Activity," *Clinical Cancer Research* 10:7207-7219, 2004.
Ekberg et al., "Post-translational modification of cyclin A1 is associated with staurosporine and TNFα induced apoptosis in leukemic cells," *Mol Cell Biochem* 320:115-124, 2009.
Farhadieh et al., "Mutant p53 and cyclin A1 protein expression in primary laryngeal squamous cell carcinomas do not correlate to second primary tumours of the head and neck," *ANZ J Surg* 79:48-54, 2009.
Fijak et al., "The testis in immune privilege," *Immunological Review* 213:66-81, 2006.
GenBank Database Accession No. NM_001111047.1, May 18, 2014, 4 pages.
GenBank Database Accession No. NP_001104517.1, May 18, 2014, 3 pages.
Ho et al., "Adoptive immunotherapy: Engineering T cell responses as biologic weapons for tumor mass destruction," *Cancer Cell* 3:431-437, 2003.
Ho et al., "In vitro methods for generating CD8+ T-cell clones for immunotherapy from the naive repertoire," *Journal of Immunological Methods* 310:40-52, 2006.
Jang et al., "Serine/Arginine Protein-Specific Kinase 2 Promotes Leukemia Cell Proliferation by Phosphorylating Acinus and Regulating Cyclin A1," *Cancer Res* 68(12):4559-4570, 2008.
Ji et al., "DNA damage response involves modulation of Ku70 and Rb functions by cyclin A1 in leukemia cells," *Int. J. Cancer* 121:706-713, 2007.
Keilholz et al., "A clinical and immunologic phase 2 trial of Wilms tumor gene product 1 (WT1) peptide vaccination in patients with AML and MDS," *Blood* 113(26):6541-6548, 2009.
Krug et al., "Cyclin A1 regulates WT1 expression in acute myeloid leukemia cells," *International Journal of Oncology* 34:129-136, 2009.
Kuball et al., "Facilitating matched pairing and expression of TCR chains introduced into human T cells," *Blood* 109(6):2331-2338, 2007.
Lapidot et al., "A cell initiating human acute myeloid leukaemia after transplantation into SCID mice," *Nature* 367:645-648, 1994.
Leen et al., "Improving T Cell Therapy for Cancer," *Annu. Rev. Immunol.* 25:243-265, 2007.
Levine et al., "Prospective Trial of Chemotherapy and Donor Leukocyte Infusions for Relapse of Advanced Myeloid Malignancies After Allogeneic Stem-Cell Transplantation," *J Clin Oncol* 20:405-412, 2002.
Li et al., "Model-based analysis of oligonucleotide arrays: Expression index computation and outlier detection," *PNAS* 98(1):31-36, 2001.
Liao et al., "Altered myelopoiesis and the development of acute myeloid leukemia in transgenic mice overexpressing cyclin A1," *PNAS* 98(12):6853-6858, 2001.
Lundegaard et al., "NetMHC-3.0: accurate web accessible predictions of human, mouse and monkey MHC class 1 affinities for peptides of length 8-11," *Nucleic Acids Research* 36:W509-W512, 2008.
Majeti et al., "Dysregulated gene expression networks in human acute myelogenous leukemia stem cells," *PNAS* 106(9):3396-3401, 2009.
Nickerson et al., "Cyclin A1-deficient mice lack histone H3 serine 10 phosphorylation and exhibit altered aurora B dynamics in late prophase of male meiosis," *Developmental Biology* 306:725-735, 2007.
Park et al., "Cancer Stem Cell-Directed Therapies: Recent Data From the Laboratory and Clinic," *Molecular Therapy* 17(2):219-230, 2009.
Rammensee et al., "SYFPEITHI: database for MHC ligands and peptide motifs," *Immunogenetics* 50:213-219, 1999.
Rezvani et al., "Leukemia-associated antigen-specific T-cell responses following combined PR1 and WT1 peptide vaccination in patients with myeloid malignancies," *Blood* 111(1):236-242, 2008.
Riddell et al., "Class I MHC-restricted cytotoxic T lymphocyte recognition of cells infected with human cytomegalovirus does not require endogenous viral gene expression," *The Journal of Immunology* 146(8):2795-2804, 1991.
Riddell et al., "The use of anti-CD3 and anti-CD28 monoclonal antibodies to clone and expand human antigen-specific T cells," *Journal of Immunological Methods* 128:189-201, 1990.
Robins et al., "Comprehensive assessment of T-cell receptor β-chain diversity in αβ cells," *Blood* 114(19):4099-4107, 2009.
Robins et al., "Overlap and Effective Size of the Human CD8+ T Cell Receptor Repertoire," *Sci Transl Med* 2, 11 pages, 2010.
Robins et al., "Ultra-sensitive detection of rare T cell clones," *Journal of Immunological Methods* 375:14-19, 2012.
Rosinski et al., "DDX3Y encodes a class I MHC-restricted H-Y antigen that is expressed in leukemic stem cells," *Blood* 111(9):4817-4826, 2008.
Schmitt et al., "T Cell Receptor Gene Therapy for Cancer," *Human Gene Therapy* 20:1240-1248, 2009.
Simpson et al., "Cancer/Testis Antigens, Gametogenesis and Cancer," *Nature Reviews* 5:615-625, 2005.
Spisak et al., "Applicability of antibody and mRNA expression microarrays for identifying diagnostic and progression markers of early and late stage colorectal cancer," *Disease Markers* 28:1-14, 2010.
Stirewalt et al., "Identification of Genes with Abnormal Expression Changes in Acute Myeloid Leukemia," *Genes, Chromosomes & Cancer* 47:8-20, 2008.
Till et al., "Adoptive immunotherapy for indolent non-Hodgkin lymphoma and mantle cell lymphoma using genetically modified autologous CD20-specific T cells," *Blood* 112(6):2261-2271, 2008.
Van Driessche et al., "Antigen-specific cellular immunotherapy of leukemia," *Leukemia* 19:1863-1871, 2005.

(56) References Cited

OTHER PUBLICATIONS

Wang et al., "Optimizing Adoptive Polyclonal T Cell Immunotherapy of Lymphomas, Using a Chimeric T Cell Receptor Possessing CD28 and CD137 Costimulatory Domains," *Human Gene Therapy* 18:712-725, 2007.

Warren et al., "Exhaustive T-cell repertoire sequencing of human peripheral blood samples reveals signatures of antigen selection and a directly measured repertoire size of at least 1 million clonotypes," *Genome Research* 21:790-797, 2011.

Wilde et al, "Dendritic cells pulsed with RNA encoding allogeneic MHC and antigen induce T cells with superior antitumor activity and higher TCR functional avidity," *Blood* 114(10):2131-2139, 2008.

Wolgemuth et al., "The A-type cyclins and the meiotic cell cycle in mammalian male germ cells," *International Journal of Andrology* 27:192-199, 2004.

Wegiel et al., "Multiple Cellular Mechanisms Related to Cyclin A1 in Prostate Cancer Invasion and Metastasis," *J Natl Cancer Inst* 100:1022-1036, 2008.

Xue et al., "Elimination of human leukemia cells in *NOD/SCID* mice by *WT1-TCR* gene-transduced human T Cells," *Blood* 106(9):3062-3067, 2005.

Yanada et al., "Efficacy of Allogeneic Hematopoietic Stem Cell Transplantation Depends on Cytogenetic Risk for Acute Myeloid Leukemia in First Disease Remission," *Cancer* 103(8) 1652-1658, 2005.

Yang et al., "Characterization of a Second Human Cyclin A That is Highly Expressed in Testis and in Several Leukemic Cell Lines," *Cancer Research* 57:913-920, 1997.

Yang et al., "Gene promoter methylation patterns throughout the process of cervical carcinogenesis," *Cellular Oncology* 32:131-143, 2010.

Lele et al., "Distinct Regions of the Mouse Cyclin A1 Gene, Ccna1, Confer Male Germ-Cell Specific Expression and Enhancer Function," *Biology of Reproduction* 71:1340-1347, 2004.

Ochsenreither et al., "Cyclin-A1 represents a new immunogenic targetable antigen expressed in acute myeloid leukemia stem cells with characteristics of a cancer-testis antigen," *Blood* 119(23):5492-5501, 2012.

Egloff et al., "Cyclin B1 and Other Cyclins as Tumor Antigens in Immunosurveillance and Immunotherapy of Cancer," *Cancer Res* 66(1):6-9, 2006.

Holm et al., "Cyclin A1 expression and associations with disease characteristics in childhood acute lymphoblastic leukemia," *Leukemia Research* 30:254-261, 2006.

Kondo et al., "Using CD40-activated B Cells to Efficiently Identify Epitopes of Tumor Antigens," *J Immunother* 32(2):157-160, 2009.

\* cited by examiner

Human Cyclin A1 Isoform c

NCBI reference sequence NP_001104517.1 GI:161377472
Polypeptide Sequence:

```
1    mhcsnpksgv vlatvargpd acqiltrapl gqdppqrtvl glltangqyr rtcgqgitri
61   rcysgsenaf ppagkkalpd cgvqeppkqg fdiymdeleq gdrdscsvre gmafedvyev
121  dtgtlksdlh flldfntvsp mlvdssllsq sedisslgtd vinvteyaee iyqylreaei
181  rhrpkahymk kqpditegmr tilvdwlvev geeyklraet lylavnfldr flscmsvlrg
241  klqlvgtaam llaskyeeiy ppevdefvyi tddtytkrql lkmehlllkv lafdltvptt
301  nqfllqylrr qgvcvrtenl akyvaelsll eadpflkylp sliaaaafcl anytvnkhfw
361  petlaaftgy slseivpcls elhkayldip hrpqqairek ykaskylcvs lmeppavlll
421  q    [SEQ ID NO:9]
```

Fig. 5A

NCBI Reference sequence NM_001111047.1 GI:161377471 Polynucleotide Sequence:

```
1    gccgcagcct gcgcagcccc gaggaccccg cgtcgctctc ccgagccagg gttctcagga
61   gcgggccgcg caggagacgt tagaggggt tgttagcggc tgttgggaga acgggtcacg
121  gaaacagtcc cttccaaagc cggggccatc gtggggtggg cgagtccgcc ctcccaggcc
181  ggggcgcgg accagagggg acgtgtgcag acggccgcgg tcagccccac ctcgcccggg
241  cggagacgca cagctggagc tggagggccg tcgcccgttg ggcctcagg ggcctgaacg
301  cccaggggtc gcggcgagtc cacccggagc gagtcagcag cccgtggagt ctgaagcaat
361  gcactgcagc aaccccaaga gtggagttgt gctggctaca gtggcccgag gtcccgatgc
421  ttgtcagata ctcaccagag ccccgctggg ccaggatccc ccgcagagga cagtgctagg
481  gctgctaact gcaaatgggc agtacaggag gacctgtggc caggggatca caagaatcag
541  gtgttattct ggatcagaaa atgccttccc tccagctgga aagaaagcac tccctgactg
601  tggggtccaa gagccccca agcaagggtt tgacatctac atggatgaac tagagcaggg
661  ggacagagac agctgctcgg tcagagaggg gatggcattt gaggatgtgt atgaagtaga
721  caccggcaca ctcaagtcag acctgcactt cctgctggat ttcaacacag tttcccctat
781  gctggtagat tcatctctcc tctcccagtc tgaagatata tccagtcttg gcacagatgt
841  gataaatgtg actgaatatg ctgaagaaat ttatcagtac cttagggaag ctgaaataag
901  gcacagaccc aaagcacact acatgaagaa gcagccagac atcacggaag gcatgcgcac
961  gattctggtg gactggctgg tggaggttgg ggaagaatat aaacttcgag cagagaccct
1021 gtatctggct gtcaacttcc tggacaggtt cctttcatgt atgtctgttc tgagagggaa
1081 actgcagctc gtaggaacag cagctatgct tttggcttcg aaatatgaag agatatatcc
1141 tcctgaagta gacgagtttg tctatatcac cgatgataca tacacaaaac gacaactgtt
1201 aaaaatggaa cacttgcttc tgaaagttct agcttttgat ctgacagtac caaccaccaa
1261 ccagtttctc cttcagtact tgaggcgaca aggagtgtgc gtcaggactg agaacctggc
1321 taagtacgta gcagagctga gtctacttga agcagatcca ttcttgaaat atcttccttc
1381 actgatagct gcagcagctt tttgcctggc aaactatact gtgaacaagc actttttggcc
1441 agaaacccctt gctgcattta cagggtattc attaagtgaa attgtgcctt gcctgagtga
1501 gcttcataaa gcgtaccttg atataccca tcgacctcag caagcaatta gggagaagta
1561 caaggcttca aagtacctgt gtgtgtccct catggagcca cctgcagttc ttcttctaca
1621 ataagtttct gaatggaagc acttccagaa cttcacctcc atatcagaag tgccaataat
1681 cgtcataggc ttctgcacgt tggatcaact aatgttgttt acaatataga tgacatttta
1741 aaaatgtaaa tgaatttagt ttcccttaga ctttagtagt ttgtaatata gtccaacatt
1801 ttttaaacaa taaactgctt gtcttatgac catgtgttag a
```

Fig. 5B

/translation=
"MHCSNPKSGVVLATVARGPDACQILTRAPLGQDPPQRTVLGLLT

ANGQYRRTCGQGITRIRCYSGSENAFPPAGKKALPDCGVQEPPKQGFDIYMDELEQGD

RDSCSVREGMAFEDVYEVDTGTLKSDLHFLLDFNTVSPMLVDSSLLSQSEDISSLGTD

VINVTEYAEEIYQYLREAEIRHRPKAHYMKKQPDITEGMRTILVDWLVEVGEEYKLRA

ETLYLAVNFLDRFLSCMSVLRGKLQLVGTAAMLLASKYEEIYPPEVDEFVYITDDTYT

KRQLLKMEHLLLKVLAFDLTVPTTNQFLLQYLRRQGVCVRTENLAKYVAELSLLEADP

FLKYLPSLIAAAAFCLANYTVNKHFWPETLAAFTGYSLSEIVPCLSELHKAYLDIPHR

PQQAIREKYKASKYLCVSLMEPPAVLLLQ    [SEQ ID NO:10]

CYCLIN A1-TARGETED T-CELL IMMUNOTHERAPY FOR CANCER

STATEMENT OF GOVERNMENT INTEREST

This invention was made with government support under CA018029 awarded by the National Institutes of Health. The government has certain rights in this invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 360056_407USPC_SEQUENCE_LISTING.txt. The text file is about 9 KB, was created on May 7, 2014, and is being submitted electronically via EFS-Web.

BACKGROUND

Technical Field

The present disclosure relates generally to methods for eliciting antigen-specific T-cell immune responses to a cancer-associated antigen. More specifically, the human cyclin A1 (CCNA1) isoform c polypeptide is herein identified as containing epitopes useful for the elicitation of specific T-cell responses against leukemic cells that overexpress CCNA1, including leukemic stem cells (LSC) and acute myeloid leukemia (AML) cells.

Description of the Related Art

In higher vertebrates the immune system distinguishes "self" from "non-self" molecular structures in cells and tissues, and provides a host organism with the means to quickly and specifically mount protective responses, such as destruction of pathogenic microorganisms and rejection of malignant tumors. Immune responses have been generally described as including humoral responses, in which antibodies specific for antigens are produced by differentiated B lymphocytes, and cell-mediated responses, in which various types of T lymphocytes eliminate antigens by a variety of mechanisms. For example, CD4 (also called CD4+) helper T-cells that are capable of recognizing specific antigens may respond by releasing soluble mediators such as cytokines to recruit additional cells of the immune system to participate in an immune response by a variety of mechanisms. CD8 (also called CD8+) cytotoxic T lymphocytes (CTL) are also capable of recognizing specific antigens and may bind to, and destroy or damage, an antigen-bearing cell or particle. In particular, cell mediated immune responses that include a cytotoxic T lymphocyte (CTL) response can be important for elimination of tumor cells and also for elimination of cells infected by pathogens, such as viruses, bacteria, or microbial parasites.

It is well established that acute myeloid leukemia (AML) is organized hierarchically, initiated and maintained by a small population of cells referred to as leukemia stem cells (LSCs) that are characterized not only by unlimited reproductive capacity but also by enhanced resistance to chemotherapy and radiation. This primitive cell population, which has been found to be negative for the expression of lineage markers and CD38 but positive for CD34, is essential for long-term engraftment of primary AML cells in NOD/SCID transplantation models (Bonnet et al., 1997 Nat Med 3 (7):730-737; Lapidot et al., 1994 Nature 367 (6464):645-648. doi: 10.1038/367645a0; Blair et al., 1998 Blood 92 (11):4325-4335). The leukemia stem cell hypothesis suggests that for a therapeutic anti-AML effect to be curative in patients, beneficial strategies would include those that efficiently eliminate the LSC compartment, which is resistant to conventional therapy approaches.

In patients with intermediate- and high-risk and/or relapsed AML, the allogeneic T-cell mediated graft-versus-leukemia effect detected in some individuals following hematopoietic stem cell transplantation (HSCT) or after infusion of donor-derived lymphocytes in the post-transplant period has been shown to be essential for the achievement of long-term complete remissions (Cornelissen et al., 2007 Blood 109 (9):3658-3666. doi:blood-2006-06-025627 [pii] 10.1182/blood-2006-06-025627; Yanada et al., 2005 Cancer 103 (8):1652-1658. doi:10.1002/cncr.20945; Breems et al., 2005 J Clin Oncol 23 (9):1969-1978. doi: JCO.2005.06.027 [pii] 10.1200/JCO.2005.06.027; Levine et al., 2002 J Clin Oncol 20 (2):405-412). However, allogeneic HSCT and unselected donor lymphocyte infusions are associated with significant toxicity due to both the conditioning regimen and the graft versus-host activity of donor lymphocytes. An alternative strategy for providing an anti-LSC cytotoxic T-lymphocyte (CTL) component to the treatment of AML patients would be to engage more targeted T-cell therapy, consisting of either the adoptive transfer of T-cells specific for, or the vaccination against, leukemia associated antigens (LAA) (Van Driessche et al., 2005 Leukemia 19 (11):1863-1871. doi: 2403930 [pii] 10.1038/sj.leu.2403930; Rezvani et al., 2008 Blood 111 (1):236-242. doi: blood-2007-08-108241 [pii] 10.1182/blood-2007-08-108241). The ability of antigen-specific T-cells to mediate elimination of AML LSCs has already been demonstrated in NOD/SCID transplantation models (Bonnet et al., 1999 Proc Natl Acad Sci USA 96 (15):8639-8644; Rosinski et al., 2008 Blood 111 (9):4817-4826. doi:blood-2007-06-096313 [pii] 10.1182/blood-2007-06-096313; Xue et al., 2005 Blood 106 (9):3062-3067. doi:2005-01-0146 [pii] 10.1182/blood-2005-01-0146).

Targeted T-cell therapy represents a potentially less toxic strategy than allogeneic hematopoietic stem cell transplantation to provide a cytotoxic anti-leukemia effect for eliminating the leukemic stem cell (LSC) compartment in acute myeloid leukemia (AML) patients. However, this strategy requires the identification of leukemia-associated antigens (LAA) that exhibit selective high expression in AML LSCs to maximize the anti-leukemic effect and minimize immune-mediated toxicities in normal tissues.

A precondition for targeted T-cell therapy achieving a maximal anti-AML effect that would be accompanied by minimal immunological toxicity is therefore to identify LAAs with high expression in and presentation by the malignant cell compartment, but without significant expression in healthy tissues. Although several AML LAAs have been described, only Wilms tumor protein 1 (WT1) has been shown to be expressed in the LSC compartment of the majority of AML patients at levels significantly higher than in physiological hematopoietic stem cells (HSGs). WT1 is currently being targeted in clinical trials both with adoptive T-cell transfer and peptide vaccination (e.g., U.S. Pat. Nos. 7,342,092; 7,608,685; 7,622,119), and objective remissions have been observed in some patients (Cheever et al., 2009 Clin Cancer Res 15 (17):5323-5337. doi:15/17/5323 [pii] 10.1158/1078-0432.CCR-09-0737; Majeti et al., 2009 Proc Natl Acad Sci USA 106 (9): 3396-3401. doi: 0900089106

[pii] 10.1073/pnas.0900089106; Xue et al., 2005 *Blood* 106 (9):3062-3067; Keilholz et al., 2009 *Blood* 113 (26):6541-6548. doi:blood-2009-02-202598 [pii] 10.1182/blood-2009-02-202598). In some AML patients, however, WT1 is not expressed, or is not detected at levels sufficiently distinct from those in HSC, or no anti-WT1 T-cell response can be elicited. WT1 expression has also been detected in several non-hematopoietic organs such as spleen, ovary and kidney, at levels that can be as high or higher than in leukemic blasts, raising concerns that WT1-targeted immunotherapy would produce toxicities in these tissues as undesirable and potentially harmful side-effects.

Clearly there is a need for additional candidate leukemia-associated antigens that are expressed in malignant cells including AML cells, and in particular in AML leukemic stem cells, to be used as immunogens for the development of highly specific, targeted immunotherapies for the treatment of cancers, including leukemias such as AML. The presently disclosed invention embodiments address this need and provide other related advantages.

BRIEF SUMMARY

The present invention provides, according to certain embodiments, an isolated peptide capable of eliciting an antigen-specific T-cell response to human cyclin A1 (CCNA1), comprising a polypeptide of no more than 20, 19, 18, 17, 16, 15, 14, 13, 12, 11, 10, 9, 8 or 7 amino acids wherein the polypeptide comprises a sequence of at least 7, 8, 9, 10, 11, 12, 13, 14, 15, 16, 17, 18, 19 or 20 contiguous amino acids from the CCNA1 amino acid sequence set forth in SEQ ID NO:9.

In another embodiment there is provided an isolated peptide capable of eliciting an antigen-specific T-cell response to human cyclin A1 (CCNA1), comprising a polypeptide of general formula I: N-X-C, [I] wherein: (a) N-X-C is a polypeptide of no more than 20, 19, 18, 17, 16, 15, 14, 13, 12, 11, 10 or 9 amino acids in which X comprises an amino acid sequence that is selected from: CCNA1(120-131) VDTGTLKSDLHF [SEQ ID NO:1], CCNA1(218-226) AETLYLAVN [SEQ ID NO:2], CCNA1(227-235) FLDRFLSCM [SEQ ID NO:3], CCNA1(253-261) ASKYEEIYP [SEQ ID NO:4], CCNA1(118-127) YEVDTGTLKS [SEQ ID NO:5], CCNA1(167-175) YAEEIYQYL [SEQ ID NO:6], CCNA1(330-339) LEADPFLKYL [SEQ ID NO:7], and CCNA1(341-351) SLIAAAAFCLA [SEQ ID NO:8], (b) N is an amino terminus of the peptide and consists of 0, 1, 2, 3, 4, 5, 6, 7, 8, 9, 10 or 11 amino acids that are independently selected from natural amino acids and non-natural amino acids, and (c) C is a carboxy terminus of the peptide and consists of 0, 1, 2, 3, 4, 5, 6, 7, 8, 9, 10 or 11 amino acids that are independently selected from natural amino acids and non-natural amino acids.

In certain further embodiments the antigen-specific T-cell response comprises major histocompatibility complex (MHC)-restricted T-cell recognition of the peptide. In certain other further embodiments the isolated peptide is capable of eliciting an antigen-specific CD8+ T-cell response to human cyclin A1 (CCNA1) in a class I human leukocyte antigen (HLA)-restricted manner. In a still further embodiment the class I HLA antigen is HLA-A*201. In certain other further embodiments the isolated peptide is capable of eliciting an antigen-specific CD4+ T-cell response to human cyclin A1 (CCNA1) in a class II human leukocyte antigen (HLA)-restricted manner. In certain other further embodiments the antigen-specific T-cell response comprises an interferon-gamma (IFN-γ) response. In certain other further embodiments the antigen-specific T-cell response comprises at least one of a CD4+ helper T lymphocyte (Th) response and a CD8+ cytotoxic T lymphocyte (CTL) response. In certain further embodiments the CTL response is directed against a CCNA1-overexpressing cell. In certain still further embodiments the CCNA1-overexpressing cell is an acute myeloid leukemia (AML) cell or a leukemic stem cell (LSC).

Turning to another embodiment, there is provided an isolated polynucleotide that encodes a peptide that is capable of eliciting an antigen-specific T-cell response to human cyclin A1 (CCNA1), the peptide comprising a polypeptide of no more than 20, 19, 18, 17, 16, 15, 14, 13, 12, 11, 10, 9, 8 or 7 amino acids wherein the polypeptide comprises a sequence of at least 7, 8, 9, 10, 11, 12, 13, 14, 15, 16, 17, 18, 19 or 20 contiguous amino acids from the CCNA1 amino acid sequence set forth in SEQ ID NO:9.

In another embodiment there is provided an isolated polynucleotide that encodes a peptide that is capable of eliciting an antigen-specific T-cell response to human cyclin A1 (CCNA1), the peptide comprising a polypeptide of general formula I: N-X-C, [I] wherein: (a) N-X-C is a polypeptide of no more than 20, 19, 18, 17, 16, 15, 14, 13, 12, 11, 10 or 9 amino acids in which X comprises an amino acid sequence that is selected from the group consisting of: CCNA1(120-131) VDTGTLKSDLHF [SEQ ID NO:1], CCNA1(218-226) AETLYLAVN [SEQ ID NO:2], CCNA1 (227-235) FLDRFLSCM [SEQ ID NO:3], CCNA1(253-261) ASKYEEIYP [SEQ ID NO:4], CCNA1(118-127) YEVDTGTLKS [SEQ ID NO:5], CCNA1(167-175) YAEEIYQYL [SEQ ID NO:6], CCNA1(330-339) LEADPFLKYL [SEQ ID NO:7], and CCNA1(341-351) SLIAAAAFCLA [SEQ ID NO:8], (b) N is an amino terminus of the peptide and consists of 0, 1, 2, 3, 4, 5, 6, 7, 8, 9, 10 or 11 amino acids that are independently selected from natural amino acids and non-natural amino acids, and (c) C is a carboxy terminus of the peptide and consists of 0, 1, 2, 3, 4, 5, 6, 7, 8, 9, 10 or 11 amino acids that are independently selected from natural amino acids and non-natural amino acids.

In certain other embodiments there is provided an immunogenic composition comprising a recombinant expression vector comprising either of the polynucleotides just described operably linked to an expression control sequence. In a further embodiment the vector is capable of delivering the polynucleotide to an antigen-presenting cell. In a still further embodiment the antigen-presenting cell is a dendritic cell. In certain other further embodiments the antigen-specific T-cell response comprises major histocompatibility complex (MHC)-restricted T-cell recognition of the peptide. In certain other further embodiments the immunogenic composition is capable of eliciting an antigen-specific CD8+ T-cell response to human cyclin A1 (CCNA1) in a class I human leukocyte antigen (HLA)-restricted manner. In a still further embodiment the class I HLA antigen is HLA-A*201. In certain other further embodiments the immunogenic composition is capable of eliciting an antigen-specific CD4+ T-cell response to human cyclin A1 (CCNA1) in a class II human leukocyte antigen (HLA)-restricted manner. In certain other further embodiments the antigen-specific T-cell response comprises an interferon-gamma (IFN-γ) response. In certain other further embodiments the antigen-specific T-cell response comprises at least one of a CD4+ helper T lymphocyte (Th) response and a CD8+ cytotoxic T lymphocyte (CTL) response. In certain further embodiments the CTL response is directed against a CCNA1-overexpressing cell, which in certain still further embodiments is an acute myeloid leukemia (AML) cell or a leukemic stem cell (LSC).

According to certain other embodiments there is provided a method of treating a condition characterized by CCNA1 overexpression in cells of a subject, comprising administering to the subject an effective amount of a composition that comprises one or more isolated peptides that are capable of eliciting an antigen-specific T-cell response to human cyclin A1 (CCNA1), each of said isolated peptides comprising a polypeptide of no more than 20, 19, 18, 17, 16, 15, 14, 13, 12, 11, 10, 9, 8 or 7 amino acids wherein the polypeptide comprises a sequence of at least 7, 8, 9, 10, 11, 12, 13, 14, 15, 16, 17, 18, 19 or 20 contiguous amino acids from the CCNA1 amino acid sequence set forth in SEQ ID NO:9.

In another embodiment there is provided a method of treating a condition characterized by CCNA1 overexpression in cells of a subject, comprising administering to the subject an effective amount of a composition that comprises one or more isolated peptides that are capable of eliciting an antigen-specific T-cell response to human cyclin A1 (CCNA1), each of said isolated peptides comprising a polypeptide of general formula I: N-X-C, [I] wherein: (a) N-X-C is a polypeptide of no more than 20, 19, 18, 17, 16, 15, 14, 13, 12, 11, 10 or 9 amino acids in which X comprises an amino acid sequence that is selected from: CCNA1(120-131) VDTGTLKSDLHF [SEQ ID NO:1], CCNA1(218-226) AETLYLAVN [SEQ ID NO:2], CCNA1(227-235) FLDRFLSCM [SEQ ID NO:3], CCNA1(253-261) ASKYEEIYP [SEQ ID NO:4], CCNA1(118-127) YEVDTGTLKS [SEQ ID NO:5], CCNA1(167-175) YAEEIYQYL [SEQ ID NO:6], CCNA1(330-339) LEADPFLKYL [SEQ ID NO:7], and CCNA1(341-351) SLIAAAAFCLA [SEQ ID NO:8], (b) N is an amino terminus of the peptide and consists of 0, 1, 2, 3, 4, 5, 6, 7, 8, 9, 10 or 11 amino acids that are independently selected from natural amino acids and non-natural amino acids, and (c) C is a carboxy terminus of the peptide and consists of 0, 1, 2, 3, 4, 5, 6, 7, 8, 9, 10 or 11 amino acids that are independently selected from natural amino acids and non-natural amino acids.

In another embodiment there is provided a method of treating a condition characterized by CCNA1 overexpression in cells of a subject, comprising administering to the subject an effective amount of a composition that comprises one or more isolated polynucleotides that each encodes a peptide that is capable of eliciting an antigen-specific T-cell response to human cyclin A1 (CCNA1), each of said peptides comprising a polypeptide of no more than 20, 19, 18, 17, 16, 15, 14, 13, 12, 11, 10, 9, 8 or 7 amino acids wherein the polypeptide comprises a sequence of at least 7, 8, 9, 10, 11, 12, 13, 14, 15, 16, 17, 18, 19 or 20 contiguous amino acids from the CCNA1 amino acid sequence set forth in SEQ ID NO:9.

In another embodiment there is provided a method of treating a condition characterized by CCNA1 overexpression in cells of a subject, comprising administering to the subject an effective amount of a composition that comprises one or more isolated polynucleotides that each encodes a peptide that is capable of eliciting an antigen-specific T-cell response to human cyclin A1 (CCNA1), each of said peptides comprising a polypeptide of general formula I: N-X-C, [I] wherein: (a) N-X-C is a polypeptide of no more than 20, 19, 18, 17, 16, 15, 14, 13, 12, 11, 10 or 9 amino acids in which X comprises an amino acid sequence that is selected from the group consisting of: CCNA1(120-131) VDTGTLKSDLHF [SEQ ID NO:1], CCNA1(218-226) AETLYLAVN [SEQ ID NO:2], CCNA1(227-235) FLDRFLSCM [SEQ ID NO:3], CCNA1(253-261) ASKYEEIYP [SEQ ID NO:4], CCNA1(118-127) YEVDTGTLKS [SEQ ID NO:5], CCNA1(167-175) YAEEIYQYL [SEQ ID NO:6], CCNA1(330-339) LEADPFLKYL [SEQ ID NO:7], and CCNA1(341-351) SLIAAAAFCLA [SEQ ID NO:8], (b) N is an amino terminus of the peptide and consists of 0, 1, 2, 3, 4, 5, 6, 7, 8, 9, 10 or 11 amino acids that are independently selected from natural amino acids and non-natural amino acids, and (c) C is a carboxy terminus of the peptide and consists of 0, 1, 2, 3, 4, 5, 6, 7, 8, 9, 10 or 11 amino acids that are independently selected from natural amino acids and non-natural amino acids.

In certain further embodiments of the above described methods the step of administering comprises administering an immunogenic composition comprising one or more recombinant expression vectors that comprise the one or more isolated polynucleotides, each of said isolated polynucleotide being operably linked to an expression control sequence. In a further embodiment the vector is capable of delivering the polynucleotide to an antigen-presenting cell. In a still further embodiment the antigen-presenting cell is a dendritic cell. In certain other further embodiments of the above described methods, the condition characterized by CCNA1 overexpression is a leukemia, which in certain further embodiments is acute myeloid leukemia.

Turning to another embodiment, there is provided a method for treating a condition characterized by CCNA1 overexpression in cells of a subject, comprising: (A) contacting in vitro, under conditions and for a time sufficient for antigen processing and presentation by antigen-presenting cells to take place, (i) a population of antigen-presenting cells that are immunocompatible with the subject, and (ii) an isolated peptide capable of eliciting an antigen-specific T-cell response to human cyclin A1 (CCNA1), comprising a polypeptide of no more than 20, 19, 18, 17, 16, 15, 14, 13, 12, 11, 10, 9, 8 or 7 amino acids wherein the polypeptide comprises a sequence of at least 7, 8, 9, 10, 11, 12, 13, 14, 15, 16, 17, 18, 19 or 20 contiguous amino acids from the CCNA1 amino acid sequence set forth in SEQ ID NO:9; and (B) administering one or a plurality of said antigen-pulsed antigen-presenting cells to the subject in an amount effective to elicit said antigen-specific T-cell response to human cyclin A1 (CCNA1).

In another embodiment there is provided a method for treating a condition characterized by CCNA1 overexpression in cells of a subject, comprising: (A) contacting in vitro, under conditions and for a time sufficient for antigen processing and presentation by antigen-presenting cells to take place, (i) a population of antigen-presenting cells that are immunocompatible with the subject, and (ii) an isolated peptide capable of eliciting an antigen-specific T-cell response to human cyclin A1 (CCNA1), comprising a polypeptide of general formula I: N-X-C, [I] wherein: (a) N-X-C is a polypeptide of no more than 20, 19, 18, 17, 16, 15, 14, 13, 12, 11, 10 or 9 amino acids in which X comprises an amino acid sequence that is selected from: CCNA1(120-131) VDTGTLKSDLHF [SEQ ID NO:1], CCNA1(218-226) AETLYLAVN [SEQ ID NO:2], CCNA1(227-235) FLDRFLSCM [SEQ ID NO:3], CCNA1(253-261) ASKYEEIYP [SEQ ID NO:4], CCNA1(118-127) YEVDTGTLKS [SEQ ID NO:5], CCNA1(167-175) YAEEIYQYL [SEQ ID NO:6], CCNA1(330-339) LEADPFLKYL [SEQ ID NO:7], and CCNA1(341-351) SLIAAAAFCLA [SEQ ID NO:8], (b) N is an amino terminus of the peptide and consists of 0, 1, 2, 3, 4, 5, 6, 7, 8, 9, 10 or 11 amino acids that are independently selected from natural amino acids and non-natural amino acids, and (c) C is a carboxy terminus of the peptide and consists of 0, 1, 2, 3, 4, 5, 6, 7, 8, 9, 10 or 11 amino acids that are independently selected from natural amino acids and non-natural amino acids, and thereby obtaining a population of antigen-pulsed antigen-presenting cells; and (B) administering one or a plurality of said antigen-pulsed antigen-presenting cells to the subject in an amount effective to elicit said antigen-specific T-cell response to human cyclin A1 (CCNA1).

In another embodiment there is provided a method for treating a condition characterized by CCNA1 overexpression in cells of a subject, comprising: (A) contacting in vitro, under conditions and for a time sufficient for antigen processing and presentation by antigen-presenting cells to take place, (i) a population of antigen-presenting cells that are immunocompatible with the subject, and (ii) a composition that comprises an isolated polynucleotide that can be expressed by said antigen-presenting cells and that encodes a peptide that is capable of eliciting an antigen-specific T-cell response to human cyclin A1 (CCNA1), the peptide comprising a polypeptide of no more than 20, 19, 18, 17, 16, 15, 14, 13, 12, 11, 10, 9, 8 or 7 amino acids wherein the polypeptide comprises a sequence of at least 7, 8, 9, 10, 11, 12, 13, 14, 15, 16, 17, 18, 19 or 20 contiguous amino acids from the CCNA1 amino acid sequence set forth in SEQ ID NO:9; and (B) administering one or a plurality of said antigen-pulsed antigen-presenting cells to the subject in an amount effective to elicit said antigen-specific T-cell response to human cyclin A1 (CCNA1).

In another embodiment there is provided a method for treating a condition characterized by CCNA1 overexpression in cells of a subject, comprising: (A) contacting in vitro, under conditions and for a time sufficient for antigen processing and presentation by antigen-presenting cells to take place, (i) a population of antigen-presenting cells that are immunocompatible with the subject, and (ii) a composition that comprises an isolated polynucleotide that can be expressed by said antigen-presenting cells and that encodes a peptide that is capable of eliciting an antigen-specific T-cell response to human cyclin A1 (CCNA1), the peptide comprising a polypeptide of general formula I: N-X-C, [I] wherein: (a) N-X-C is a polypeptide of no more than 20, 19, 18, 17, 16, 15, 14, 13, 12, 11, 10 or 9 amino acids in which X comprises an amino acid sequence that is selected from: CCNA1(120-131) VDTGTLKSDLHF [SEQ ID NO:1], CCNA1(218-226) AETLYLAVN [SEQ ID NO:2], CCNA1 (227-235) FLDRFLSCM [SEQ ID NO:3], CCNA1(253-261) ASKYEEIYP [SEQ ID NO:4], CCNA1(118-127) YEVDTGTLKS [SEQ ID NO:5], CCNA1(167-175) YAEEIYQYL [SEQ ID NO:6], CCNA1(330-339) LEADPFLKYL [SEQ ID NO:7], and CCNA1(341-351) SLIAAAAFCLA [SEQ ID NO:8], (b) N is an amino terminus of the peptide and consists of 0, 1, 2, 3, 4, 5, 6, 7, 8, 9, 10 or 11 amino acids that are independently selected from natural amino acids and non-natural amino acids, and (c) C is a carboxy terminus of the peptide and consists of 0, 1, 2, 3, 4, 5, 6, 7, 8, 9, 10 or 11 amino acids that are independently selected from natural amino acids and non-natural amino acids, and thereby obtaining a population of antigen-pulsed antigen-presenting cells; and (B) administering one or a plurality of said antigen-pulsed antigen-presenting cells to the subject in an amount effective to elicit said antigen-specific T-cell response to human cyclin A1 (CCNA1).

In certain further embodiments of the just-described methods, the method further comprises a step of expanding the number of antigen-presenting cells by culturing the antigen-presenting cells after the step of contacting and prior to the step of administering. In certain other further embodiments of the just-described methods, the method further comprises (C) (1) contacting the antigen-pulsed antigen-presenting cells with one or a plurality of immunocompatible T-cells after step (A), under conditions and for a time sufficient to generate CCNA1-specific T-cells, and (2) adoptively transferring the CCNA1-specific T-cells to the subject. In certain still further embodiments, step (B) is omitted.

In certain other further embodiments of the just-described methods, the method further comprises (C) (1) contacting the antigen-pulsed antigen-presenting cells with one or a plurality of immunocompatible T-cells after step (A), under conditions and for a time sufficient to generate CCNA1-specific T-cells, (2) expanding the CCNA1-specific T-cells to obtain one or more clones of said CCNA1-specific T-cells in amounts sufficient for T-cell receptor structural characterization, (3) determining a T-cell receptor polypeptide encoding nucleic acid sequence for one or more of said CCNA1-specific T-cells, (4) transfecting an adoptive transfer T-cell population with at least one T-cell receptor polypeptide encoding nucleic acid having a sequence determined in (3) to obtain engineered CCNA1-specific adoptive transfer T-cells, and 4) adoptively transferring the engineered CCNA1-specific adoptive transfer T-cells to the subject. In certain still further embodiments, step (B) is omitted.

These and other aspects and embodiments of the herein described invention will be evident upon reference to the following detailed description and attached drawings. All of the U.S. patents, U.S. patent application publications, U.S. patent applications, foreign patents, foreign patent applications and non-patent publications referred to in this specification and/or listed in the Application Data Sheet are incorporated herein by reference in their entirety, as if each was incorporated individually. Aspects and embodiments of the invention can be modified, if necessary, to employ concepts of the various patents, applications and publications to provide yet further embodiments.

BRIEF DESCRIPTION OF THE SEVERAL VIEWS OF THE DRAWINGS

FIG. 5 shows human cyclin A1 (CCNA1) isoform c amino acid (FIG. 5A)(SEQ ID NO:9) and encoding polynucleotide (FIG. 5B) (SEQ ID NO:10) sequences.

DETAILED DESCRIPTION

Figure 1:
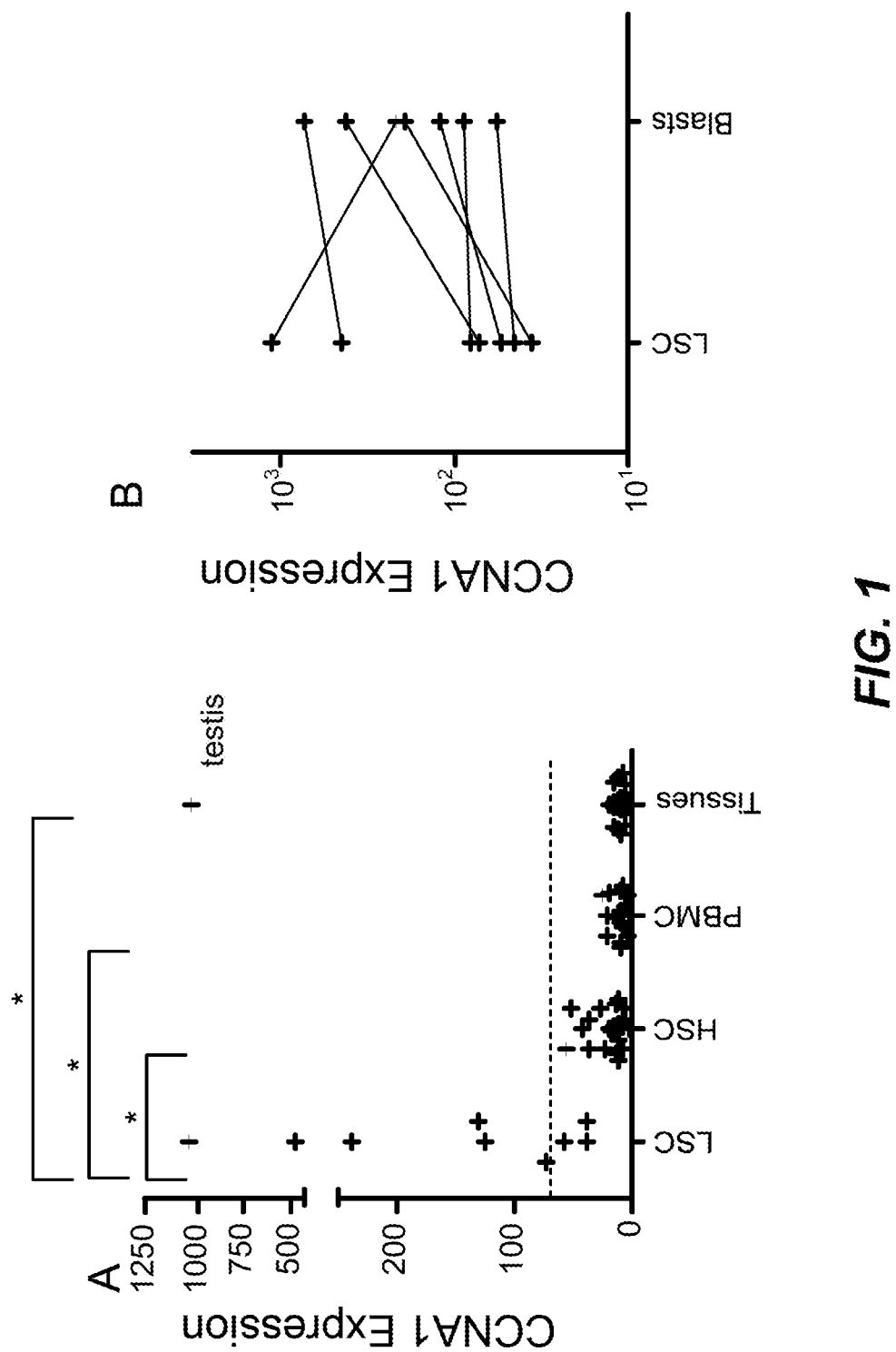
FIG. 1 shows model-based expression of probe set 205899_at representing CCNA1: (A) Expression in AML LSC compared to HSCs/CD34+BM mononuclear cells, PBMCs and non-hematopoietic tissues, * p<0.001 (explorative), (B) expression in AML LSCs and corresponding blasts.

Embodiments of the present invention as disclosed herein relate to the unexpected discoveries that the intracellular protein human cyclin A1 (CCNA1, e.g., NCBI reference sequence (isoform c) NP_001104517.1, GI:161377472; NM_001111047.1 GI:161377471) is a leukemia-associated antigen (LAA), and that certain specific short peptides of at least 9, 10, 11 or 12 contiguous amino acids from the CCNA1 sequence contain immunogenic epitopes that are recognized by T-cells in a major histocompatibility complex (MHC) antigen-restricted (e.g., HLA-restricted) manner. Surprisingly, despite the occurrence of CCNA1 as an intracellular protein with a limited cell type expression pattern and tissue distribution, as disclosed herein CCNA1 is a cancer associated antigen and CCNA1-derived peptides are capable of eliciting CCNA1-specific T-cell responses. In certain preferred embodiments the herein described CCNA1-derived peptides are capable of eliciting CCNA1-specific cytotoxic lymphocyte (CTL) responses by class I HLA-restricted CD8$^+$ T-cells.

As described in greater detail below, the intracellular protein CCNA1, which has been previously shown in murine studies to contribute to leukemogenesis and to promote cell proliferation and survival, has been detected in the LSC compartment of approximately 50% of all AML patients, and is not detectable in other tissues with the exception of the testis. Using dendritic cells pulsed with a peptide library spanning the entire CCNA1 isoform c that is found in LSC, T-cells were generated that were capable of responding to many different CCNA1-derived oligopeptides. Eight CCNA1-derived peptides were identified that were immunogenic for T-cells, two of which were more fully characterized as immunogenic, HLA A*0201-restricted epitopes of CCNA1. T-cell clones specific for these epitopes recognized peptide-pulsed target cells and also exhibited cytotoxicity against an HLA A*0201-positive AML line, THP-1, which endogenously expresses CCNA1.

The compositions and methods described herein will in certain embodiments have therapeutic utility for the treatment of diseases and conditions associated with CCNA1 overexpression (e.g., detectable CCNA1 expression at a level that is greater in magnitude, in a statistically significant manner, than the level of CCNA1 expression that is detectable in a normal or disease-free cell). Such diseases include various forms of cancer and include without limitation hematologic malignancies that arise from CCNA1 overexpressing leukemia stem cells (LSC), for instance, acute myeloid leukemia (AML). Non-limiting examples of these and related uses are described herein and include in vitro and in vivo stimulation of CCNA1 antigen-specific T-cell responses, such as by the use of immunogenic CCNA1 peptides in peptide-based vaccines, the use of vaccines that are based on engineered polynucleotides that encode such immunogenic CCNA1 peptides or additional immunogenic peptides present in CCNA1, or the use of larger fragments or the whole CCNA1 protein to induce T-cell responses.

Also contemplated, by way of illustration and not limitation, are immunotherapeutic protocols involving the adoptive transfer to a subject (e.g., an AML patient) of antigen-presenting cells that have been pulsed in vitro with immunogenic CCNA1 peptides or with CCNA1 protein or that have been modified to express immunogenic CCNA1 peptides, and/or adoptive transfer to the subject of CCNA-1-specific T-cells that have been induced in vitro by exposure to antigen-presenting cells that have been pulsed in vitro with immunogenic CCNA1 peptides. Principles of antigen processing by antigen presenting cells (APC) such as dendritic cells, macrophages, lymphocytes and other cell types, and of antigen presentation by APC to T-cells, including major histocompatibility complex-(MHC) restricted presentation between immunocompatible (e.g., sharing at least one allelic form of an MHC gene that is relevant for antigen presentation) APC and T-cells, are well established (see, e.g., Murphy, Janeway's Immunobiology (8$^{th}$ Ed.) 2011 Garland Science, NY; chapters 6, 9 and 16). Adoptive transfer protocols using unselected or selected T-cells are known in the art (e.g., US2011/0052530, US2010/0310534; Ho et al., 2006 *J. Imm. Meth.* 310:40; Ho et al., 2003 Canc. Cell 3:431) and may be modified according to the teachings herein for use with transfer cell populations containing T-cells that are specifically induced by one or more immunogenic CCNA1-derived T-cell epitope-containing peptides.

As another non-limiting example, certain presently disclosed embodiments contemplate cloning CCNA1-reactive T-cells that have been induced in vitro by exposure to antigen-presenting cells that have been pulsed in vitro with immunogenic CCNA1 peptides, and from such T-cells identifying and cloning the functional (e.g., productively rearranged) T-cell receptor (TCR) encoding genes, which may then be used to transfect/transduce a T-cell population for adoptive transfer into subjects. Recent advances in TCR sequencing have been described (e.g., Robins et al., 2009 *Blood* 114:4099; Robins et al., 2010 *Sci. Translat. Med.* 2:47ra64, PMID: 20811043; Robins et al. 2011 (September 10) *J. Imm. Meth.* Epub ahead of print, PMID: 21945395; Warren et al., 2011 *Genome Res.* 21:790) and may be employed in the course of practicing these embodiments according to the present disclosure. Similarly, methods for transfecting/transducing T-cells with desired nucleic acids have been described (e.g., US2004/0087025) as have adoptive transfer procedures using T-cells of desired antigen-specificity (e.g., Schmitt et al., 2009 *Hum. Gen.* 20:1240; Dossett et al., 2009 *Mol. Ther.* 17:742; Till et al., 2008 *Blood* 112:2261; Wang et al., 2007 *Hum. Gene Ther.* 18:712; Kuball et al., 2007 *Blood* 109:2331; US2011/0243972; US2011/0189141; Leen et al., 2007 *Ann. Rev. Immunol.* 25:243), such that adaptation of these methodologies to the presently disclosed embodiments is contemplated, based on the teachings herein, including those that are directed to specific CCNA1-derived peptides that are capable of eliciting antigen-specific T-cell responses.

Presently disclosed T-cell immunogens, for use in inducing or eliciting immune responses against inappropriately CCNA1-overexpressing cells such as cancer cells, include isolated peptides that are capable of eliciting an antigen-specific T-cell response to human cyclin A1 (CCNA1), each peptide comprising at least one of a full length CCNA1 polypeptide or a CCNA1-derived polypeptide of no more than 400, 350, 300, 250, 200, 150, 125, 100, 80, 70, 60, 50, 40, 30, 25, 20, 19, 18, 17, 16, 15, 14, 13, 12, 11, 10, 9, 8 or 7 amino acids wherein the polypeptide comprises a sequence of at least 7, 8, 9, 10, 11, 12, 13, 14, 15, 16, 17, 18, 19 or 20, or 400, 350, 300, 250, 200, 150, 125, 100, 80, 70, 60, 50, 40, 30, 25 contiguous amino acids from the CCNA1 amino acid sequence set forth in SEQ ID NO:9. CCNA1-overexpressing cells cancer cells include cells of hematologic malignancies such as lymphoma and leukemia, and in particular, leukemia stem cells and/or acute myeloid leukemia cells.

According to certain presently disclosed embodiments, an isolated peptide capable of eliciting an antigen-specific T-cell response to human cyclin A1 (CCNA1), comprises a polypeptide of general formula I:

N-X-C                                                [I]

wherein:
(a) N-X-C is a polypeptide of no more than 20, 19, 18, 17, 16, 15, 14, 13, 12, 11, 10 or 9 amino acids in which X comprises an amino acid sequence that is selected from:

```
                              [SEQ ID NO: 1]
CCNA1(120-131) VDTGTLKSDLHF,

[SEQ ID NO: 2]
CCNA1(218-226) AETLYLAVN,

[SEQ ID NO: 3]
CCNA1(227-235) FLDRFLSCM,

[SEQ ID NO: 4]
CCNA1(253-261) ASKYEEIYP,

[SEQ ID NO: 5]
CCNA1(118-127) YEVDTGTLKS,

[SEQ ID NO: 6]
CCNA1(167-175) YAEEIYQYL,

[SEQ ID NO: 7]
CCNA1(330-339) LEADPFLKYL,
and

[SEQ ID NO: 8]
CCNA1(341-351) SLIAAAAFCLA,
``` and also wherein:
(b) N is an amino terminus of the peptide and consists of 0, 1, 2, 3, 4, 5, 6, 7, 8, 9, 10 or 11 amino acids that are independently selected from natural and non-natural amino acids amino acids, and wherein (c) C is a carboxy terminus of the peptide and consists of 0, 1, 2, 3, 4, 5, 6, 7, 8, 9, 10 or 11 amino acids that are independently selected from natural and non-natural amino acids amino acids.

Accordingly in these and other embodiments it will be appreciated that the amino terminus of certain CCNA1-derived peptides disclosed herein as comprising T-cell immunogenic epitopes may consist of 1-11 independently selected natural or non-natural amino acids, and/or that in certain embodiments the carboxy terminus of certain such peptides may consist of 1-11 independently selected natural or non-natural amino acids, where such amino and carboxy termini may have any sequence so long as the isolated peptide is of no more than 9-20 amino acids and comprises N-X-C as recited herein, and is capable of specifically eliciting an antigen-specific T-cell response to human cyclin A1 (CCNA1).

Disclosed herein are a number of representative CCNA1-derived peptides that comprise N-X-C according to formula [I] as recited herein, and that are capable of specifically eliciting an antigen-specific T-cell response to human cyclin A1 (CCNA1). The presently contemplated invention embodiments, however, are not intended to be so limited such that in view of the present disclosure those familiar with the art will be able readily to make and use additional CCNA1 peptides (and variants thereof) that are immunogenic for T-cells.

For example, determination of the three-dimensional structures of representative immunogenic CCNA1-derived peptides bearing T-cell epitopes as described herein may be made through routine methodologies such that substitution of one or more amino acids with selected natural or non-natural amino acids can be virtually modeled for purposes of determining whether a so derived structural variant retains the space-filling, charge, hydrophilic and/or hydrophobic properties of presently disclosed species, including modeling of potential peptide affinity interactions with MHC peptide-binding grooves (e.g., BIMAS molecular modeling software, described by Parker et al., *J. Immunol.* 152:163, 1994; Tsites database, Feller et al. 1991 *Nature* 349:720; Rothbard et al., 1988 *EMBO J.* 7:93-100; Deavin et al., 1996 *Mol. Immunol.* 33:145-155; and other HLA peptide binding prediction analyses). See also, for instance, Donate et al., 1994 *Prot. Sci.* 3:2378; Bradley et al., *Science* 309: 1868-1871 (2005); Schueler-Furman et al., *Science* 310:638 (2005); Dietz et al., *Proc. Nat. Acad. Sci. USA* 103:1244 (2006); Dodson et al., *Nature* 450:176 (2007); Qian et al., *Nature* 450:259 (2007); Raman et al. *Science* 327:1014-1018 (2010). These and other references describe computer algorithms that may be used for related embodiments, such as for rational design of variants of the CCNA1-derived peptides bearing T-cell epitopes as provided herein (e.g., SEQ ID NOS:1-8), for instance, by allowing for determination of atomic dimensions from space-filling models (van der Waals radii) of energy-minimized conformations.

In view of the present disclosure that the CCNA1 polypeptide and CCNA1-derived peptides contain immunogenic epitopes, e.g., the molecular structures that are specifically recognized by T-cells via the T cell receptor (TCR) including via MHC-restricted T-cell recognition, it is thus expressly contemplated that alterations (e.g., increases or decreases that are detectable with statistical significance) in the immunogenicity of any given epitope-bearing CCNA1 peptide may be introduced by structural modification, for example, to obtain immunogenic CCNA1 peptide-derived variants. Means for enhancing the immunogenicity of a peptide-defined epitope are known in the art, and may include the altered peptide ligand (APL) approach by which structural modifications are made to a given peptide. Peptide variants of enhanced immunogenicity have been generated as APLs, as described in other antigen systems, for instance, by Abdul-Alim et al. (2010 *J. Immunol.* 184:6514); Douat-Casassus et al. (2007 *J. Med. Chem.* 50:1598); Carrabba et al. (2003 *Canc. Res.* 63:1560); and Shang et al. (2009 *Eur. J. Immunol.* 39:2248). Accordingly it will be appreciated from the present disclosure that CCNA1 peptide sequences include a large number of immunogenic epitopes for T-cells, such that CCNA1 fragments (e.g., sequences of at least 7, 8, 9, 10, 11, 12, 13, 14, 15, 16, 17, 18, 19 or 20, or 400, 350, 300, 250, 200, 150, 125, 100, 80, 70, 60, 50, 40, 30, 25 contiguous amino acids from the CCNA1 amino acid sequence set forth in SEQ ID NO:9) and/or variants as provided herein (including APLs) may be encompassed within certain embodiments.

Some additional non-limiting examples of computer algorithms that may be used for these and related embodiments, such as for rational design of variants of the herein described CCNA1 immunogenic peptide epitopes (e.g., SEQ ID NOS: 1-8), include NAMD, a parallel molecular dynamics code designed for high-performance simulation of large biomolecular systems, and VMD which is a molecular visualization program for displaying, animating, and analyzing large biomolecular systems using 3-D graphics and built-in scripting (see Phillips, et al., *Journal of Computational Chemistry*, 26:1781-1802, 2005; Humphrey, et al., "VMD—Visual Molecular Dynamics", *J. Molec. Graphics*, 1996, vol. 14, pp. 33-38; see also the website for the Theoretical and Computational Biophysics Group, University of Illinois at Urbana-Champagne, at ks.uiuc.edu/Research/vmd/). Many other computer programs are known in the art and available to the skilled person and allow for determining atomic dimensions from space-filling models (van der Waals radii) of energy-minimized conformations; for example, GRID, which seeks to determine regions of high affinity for different chemical groups, thereby enhancing binding; Monte Carlo searches, which calculate mathematical alignment; and CHARMM (Brooks et al. (1983) *J. Comput. Chem.* 4:187-217) and AMBER (Weiner et al (1981) *J. Comput. Chem.* 106: 765), which assess force field calculations, and analysis (see also, Eisenfield et al. (1991) *Am. J. Physiol.* 261:C376-386; Lybrand (1991) *J. Pharm. Belg.* 46:49-54; Froimowitz (1990) *Biotechniques* 8:640-644; Burbam et al. (1990) *Proteins* 7:99-111; Pedersen (1985) *Environ. Health Perspect.* 61:185-190; and Kini et al. (1991) *J. Biomol. Struct. Dyn.* 9:475-488). A variety of appropriate computational computer programs are also commercially available, such as from Schrödinger (Munich, Germany).

"Natural or non-natural amino acid" includes any of the common naturally occurring amino acids which serve as building blocks for the biosynthesis of peptides, polypeptides and proteins (e.g., alanine, cysteine, aspartic acid, glutamic acid, phenylalanine, glycine, histidine, isoleucine, lysine, leucine, methionine, asparagine, proline, glutamine, arginine, serine, threonine, valine, tryptophan, tyrosine) and also includes modified, derivatized, enantiomeric, rare and/or unusual amino acids, whether naturally occurring or synthetic, for instance, hydroxyproline, hydroxylysine, desmosine, isodesmosine, ε-N-methyllysine, ε-N-trimethyllysine, methylhistidine, dehydrobutyrine, dehydroalanine, α-aminobutyric acid, β-alanine, γ-aminobutyric acid, homocysteine, homoserine, citrulline, ornithine and other amino acids that may be isolated from a natural source and/or that may be chemically synthesized, for instance, as may be found in *Proteins, Peptides and Amino Acids Sourcebook* (White, J. S. and White, D.C., 2002 Humana Press, Totowa, N.J.) or in *Amino Acid and Peptide Synthesis* (Jones, J., 2002 Oxford Univ. Press USA, New York) or in *Unnatural Amino Acids, ChemFiles* Vol. 1, No. 5 (2001 Fluka Chemie GmbH; Sigma-Aldrich, St. Louis, Mo.) or in *Unnatural Amino Acids II, ChemFiles Vol. 2, No. 4* (2002 Fluka Chemie GmbH; Sigma-Aldrich, St. Louis, Mo.). Additional descriptions of natural and/or non-natural amino acids may be found, for example, in Kotha, 2003 *Acc. Chem. Res.* 36:342; Maruoka et al., 2004 *Proc. Nat. Acad. Sci. USA* 101:5824; Lundquist et al., 2001 *Org. Lett.* 3:781; Tang et al., 2002 *J. Org. Chem.* 67:7819; Rothman et al., 2003 *J. Org. Chem.* 68:6795; Krebs et al., 2004 *Chemistry* 10:544; Goodman et al., 2001 *Biopolymers* 60:229; Sabat et al., 2000 *Org. Lett.* 2:1089; Fu et al., 2001 *J. Org. Chem.* 66:7118; and Hruby et al., 1994 *Meths. Mol. Biol.* 35:249. The standard three-letter abbreviations and 1-letter symbols are used herein to designate natural and non-natural amino acids.

Other non-natural amino acids or amino acid analogues are known in the art and include, but are not limited to, non-natural L or D derivatives (such as D-amino acids present in peptides), fluorescent labeled amino acids, as well as specific examples including O-methyl-L-tyrosine, L-3-(2-naphthyl)alanine, 3-methyl-phenylalanine, 3-idio-tyrosine, O-propargyl-tyrosine, homoglutamine, an O-4-allyl-L-tyrosine, a 4-propyl-L-tyrosine, a 3-nitro-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-acetyl-L-phenylalanine, an m-acetyl-L-phenylalanine, selenomethionine, telluromethionine, selenocysteine, an alkyne phenylalanine, an O-allyl-L-tyrosine, an O-(2-propynyl)-L-tyrosine, a p-ethylthiocarbonyl-L-phenylalanine, a p-(3-oxobutanoyl)-L-phenylalanine, a p-benzoyl-L-phenylalanine, an L-phosphoserine, a phosphonoserine, a phosphonotyrosine, homopropargylglycine, azidohomoalanine, a p-iodo-phenylalanine, a p-bromo-L-phenylalanine, dihydroxy-phenylalanine, dihydroxyl-L-phenylalanine, a p-nitro-L-phenylalanine, an m-methoxy-L-phenylalanine, a p-iodo-phenylalanine, a p-bromophenylalanine, a p-amino-L-phenylalanine, and an isopropyl-L-phenylalanine, trifluoroleucine, norleucine ("Nle"), D-norleucine ("dNle" or "D-Nle"), 5-fluoro-tryptophan, para-halo-phenylalanine, homo-phenylalanine ("homo-Phe"), seleno-methionine, ethionine, S-nitroso-homocysteine, thia-proline, 3-thienyl-alanine, homo-allyl-glycine, trifluoroisoleucine, trans and cis-2-amino-4-hexenoic acid, 2-butynyl-glycine, allyl-glycine, para-azido-phenylalanine, para-cyano-phenylalanine, para-ethynyl-phenylalanine, hexafluoroleucine, 1,2,4-triazole-3-alanine, 2-fluoro-histidine, L-methyl histidine, 3-methyl-L-histidine, β-2-thienyl-L-alanine, β-(2-thiazolyl)-DL-alanine, homopropargylglycine (HPG) and azido-homoalanine (AHA) and the like.

In certain embodiments a natural or non-natural amino acid may be present that comprises an aromatic side chain, as found, for example, in phenylalanine or tryptophan or analogues thereof including in other natural or non-natural amino acids based on the structures of which the skilled person will readily recognize when an aromatic ring system is present, typically in the form of an aromatic monocyclic or multicyclic hydrocarbon ring system consisting only of hydrogen and carbon and containing from 6 to 19 carbon atoms, where the ring system may be partially or fully saturated, and which may be present as a group that includes, but need not be limited to, groups such as fluorenyl, phenyl and naphthyl.

In certain embodiments a natural or non-natural amino acid may be present that comprises a hydrophobic side chain as found, for example, in alanine, valine, isoleucine, leucine, proline, phenylalanine, tryptophan or methionine or analogues thereof including in other natural or non-natural amino acids based on the structures of which the skilled person will readily recognize when a hydrophobic side chain (e.g., typically one that is non-polar when in a physiological milieu) is present. In certain embodiments a natural or non-natural amino acid may be present that comprises a basic side chain as found, for example, in lysine, arginine or histidine or analogues thereof including in other natural or non-natural amino acids based on the structures of which the skilled person will readily recognize when a basic (e.g., typically polar and having a positive charge when in a physiological milieu) is present.

Polypeptides disclosed herein may include L- and/or D-amino acids so long as the biological activity (e.g., CCNA1-specific immunogenicity for T-cells) of the polypeptide is maintained. The isolated CCNA1-derived polypeptides may comprise in certain embodiments any of a variety of known natural and artificial post-translational or post-synthetic covalent chemical modifications by reactions that may include glycosylation (e.g., N-linked oligosaccharide addition at asparagine residues, O-linked oligosaccharide addition at serine or threonine residued, glycation, or the like), fatty acylation, acetylation, PEGylation, and phosphorylation. Polypeptides herein disclosed may further include analogs, alleles and allelic variants which may contain amino acid deletions, or additions or substitutions of one or more amino acid residues with other naturally occurring amino acid residues or non-natural amino acid residues.

Peptide and non-peptide analogs may be referred to as peptide mimetics or peptidomimetics, and are known in the pharmaceutical industry (Fauchere, *J. Adv. Drug Res.* 15:29 (1986); Evans et al. *J. Med. Chem.* 30: 1229 (1987)). These compounds may contain one or more non-natural amino acid residue(s), one or more chemical modification moieties (for example, glycosylation, pegylation, fluorescence, radioactivity, or other moiety), and/or one or more non-natural peptide bond(s) (for example, a reduced peptide bond: —$CH_2$—$NH_2$—). Peptidomimetics may be developed by a variety of methods, including by computerized molecular modeling, random or site-directed mutagenesis, PCR-based strategies, chemical mutagenesis, and others.

The term "isolated" means that the material is removed from its original environment (e.g., the natural environment if it is naturally occurring). For example, a naturally occurring nucleic acid or polypeptide present in a living animal is not isolated, but the same nucleic acid or polypeptide, separated from some or all of the co-existing materials in the natural system, is isolated. Such nucleic acid could be part of a vector and/or such nucleic acid or polypeptide could be part of a composition (e.g., a cell lysate), and still be isolated in that such vector or composition is not part of the natural environment for the nucleic acid or polypeptide. The term "gene" means the segment of DNA involved in producing a polypeptide chain; it includes regions preceding and following the coding region "leader and trailer" as well as intervening sequences (introns) between individual coding segments (exons).

Certain embodiments relate to nucleic acids that encode the polypeptides contemplated herein, for instance, CCNA1-derived polypeptides that contain epitopes recognized by, and immunogenic for, T-cells. As one of skill in the art will recognize, a nucleic acid may refer to a single and/or a double stranded DNA, cDNA or RNA in any form, and may include a positive and a negative strand of the nucleic acid which complement each other, including anti-sense DNA, cDNA and RNA. Also included are siRNA, microRNA, RNA-DNA hybrids, ribozymes, and other various naturally occurring or synthetic forms of DNA or RNA.

Certain embodiments include nucleic acids contained in a vector. One of skill in the art can readily ascertain suitable vectors for use with certain herein disclosed embodiments. A typical vector may comprise a nucleic acid molecule capable of transporting another nucleic acid to which it has been linked, or which is capable of replication in a host organism. Some examples of vectors include plasmids, viral vectors, cosmids, and others. Some vectors may be capable of autonomous replication in a host cell into which they are introduced (e.g. bacterial vectors having a bacterial origin of replication and episomal mammalian vectors), whereas other vectors may be integrated into the genome of a host cell upon introduction into the host cell and thereby replicate along with the host genome. Additionally, some vectors are capable of directing the expression of genes to which they are operatively linked (these vectors may be referred to as "expression vectors"). According to related embodiments, it is further understood that, if one or more agents (e.g., polynucleotides encoding CCNA1-derived immunogenic peptide epitopes, or variants thereof, as described herein) is co-administered to a subject, that each agent may reside in separate or the same vectors, and multiple vectors (each containing a different agent the same agent) may be introduced to a cell or cell population or administered to a subject.

In certain embodiments, the nucleic acid encoding the herein described CCNA1-derived polypeptides that contain epitopes recognized by and immunogenic for T-cells, may be operatively linked to certain elements of a vector. For example, polynucleotide sequences that are needed to effect the expression and processing of coding sequences to which they are ligated may be operatively linked. Expression control sequences may include appropriate transcription initiation, termination, promoter and enhancer sequences; efficient RNA processing signals such as splicing and polyadenylation signals; sequences that stabilize cytoplasmic mRNA; sequences that enhance translation efficiency (i.e. Kozak consensus sequences); sequences that enhance protein stability; and possibly sequences that enhance protein secretion. Expression control sequences may be operatively linked if they are contiguous with the gene of interest and expression control sequences that act in trans or at a distance to control the gene of interest.

In particular embodiments, the recombinant expression vector is delivered to an appropriate cell, for example, an antigen-presenting cell i.e., a cell that displays a peptide/MHC complex on its cell surface (e.g., a dendritic cell) that will induce the desired CCNA1-specific cell-mediated immune response, such as CD8 T-cell response including a cytotoxic T lymphocyte (CTL) response. The recombinant expression vectors may therefore also include, for example, lymphoid tissue-specific transcriptional regulatory elements (TRE) such as a B lymphocyte, T lymphocyte, or dendritic cell specific TRE. Lymphoid tissue specific TRE are known in the art (see, e.g., Thompson et al., *Mol. Cell. Biol.* 12, 1043-53 (1992); Todd et al., *J. Exp. Med.* 177, 1663-74 (1993); Penix et al., *J. Exp. Med.* 178:1483-96 (1993)).

In certain configurations, recombinant expression vectors may contain polynucleotide sequences that encode dendritic cell (DC) maturation/stimulatory factors. Exemplary stimulatory molecules include GM-CSF, IL-2, IL-4, IL-6, IL-7, IL-15, IL-21, IL-23, TNFα, B7.1, B7.2, 4-1BB, CD40 ligand (CD40L), drug-inducible CD40 (iCD40), and the like. These polynucleotides are typically under the control of one or more regulatory elements that direct the expression of the coding sequences in dendritic cells. Maturation of dendritic cells contributes to successful vaccination (see, e.g., Banchereau et al., *Nat. Rev. Immunol.* 5:296-306 (2005); Schuler et al., *Curr. Opin. Immunol.* 15:138-147 (2003); Figdor et al., *Nat. Med.* 10:475-480 (2004)). Maturation can transform DCs from cells actively involved in antigen capture into cells specialized for T-cell priming. For example, engagement of CD40 by CD40L on CD4-helper T-cells is an important signal for DC maturation, resulting in potent activation of CD8+ T-cells. Such stimulatory molecules are also referred to as maturation factors or maturation stimulatory factors.

In addition to vectors, certain embodiments relate to host cells that comprise the vectors that are presently disclosed. One of skill in the art readily understands that many suitable host cells are available in the art. A host cell may include any individual cell or cell culture which may receive a vector or the incorporation of nucleic acids and/or proteins, as well as any progeny cells. The term also encompasses progeny of the host cell, whether genetically or phenotypically the same or different. Suitable host cells may depend on the vector and may include mammalian cells, animal cells, human cells, simian cells, insect cells, yeast cells, and bacterial cells. These cells may be induced to incorporate the vector or other material by use of a viral vector, transformation via calcium phosphate precipitation, DEAE-dextran, electroporation, microinjection, or other methods. For example, See Sambrook et al. *Molecular Cloning: A Laboratory Manual* 2d ed. (Cold Spring Harbor Laboratory, 1989).

In certain embodiments, immunogenic variants are provided of the herein described CCNA1-derived polypeptides that contain epitopes recognized by, and immunogenic for, T-cells; these variants include polypeptide species that have one or more amino acid substitutions, insertions, or deletions in the amino acid sequence relative to the sequences of formula (I) or SEQ ID NOS:1-8 as presented herein. Conservative substitutions of amino acids are well known and may occur naturally in the polypeptide or may be introduced when the polypeptide is recombinantly produced. Amino acid substitutions, deletions, and additions may be introduced into a polypeptide using well-known and routinely practiced mutagenesis methods (see, e.g., Sambrook et al. *Molecular Cloning: A Laboratory Manual*, 3d ed., Cold Spring Harbor Laboratory Press, NY 2001)). Oligonucleotide-directed site-specific (or segment specific) mutagenesis procedures may be employed to provide an altered polynucleotide that has particular codons altered according to the substitution, deletion, or insertion desired. Deletion or truncation variants of specific peptides that may be used as immunogens may also be constructed by using convenient restriction endonuclease sites adjacent to the desired deletion. Subsequent to restriction, overhangs may be filled in and the DNA re-ligated. Alternatively, random mutagenesis techniques, such as alanine scanning mutagenesis, error prone polymerase chain reaction mutagenesis, and oligonucleotide-directed mutagenesis may be used to prepare immunogen polypeptide variants (see, e.g., Sambrook et al., supra). Species (or variants) of a particular CCNA1-derived immunogen (or polypeptide fragment thereof) may include a polypeptide immunogen that has at least 85%, 90%, 95%, or 99% amino acid sequence identity to any of the exemplary amino acid sequences disclosed herein (e.g., SEQ ID NOS:1-8, or polypeptides of no more than 20, 19, 18, 17, 16, 15, 14, 13, 12, 11, 10 or 9 amino acids in which at least one of SEQ ID NOS:1-8 may be present).

These CCNA1-derived peptide immunogen variants retain one or more biological activities or functions of the respective CCNA1-derived peptide that is immunogenic for T-cells as described herein (e.g., SEQ ID NOS:1-8). In particular, such immunogens that are variants of a herein described CCNA1-derived peptide retain, in a statistically, clinically, or biologically significant manner, the capability to induce a T-cell response (including a cytotoxic T lymphocyte response). Given the many molecular biology, protein expression, and protein isolation techniques and methods routinely practiced in the art for introducing mutations in a polypeptide, preparing polypeptide fragments, isolating the fragments and variants, and analyzing such products, immunogenic CCNA1 polypeptide variants and fragments thereof having the desired biological activities can be made readily and without undue experimentation based on the disclosure herein.

A variety of criteria known to persons skilled in the art indicate whether an amino acid that is substituted at a particular position in a peptide or polypeptide is conservative (or similar). For example, a similar amino acid or a conservative amino acid substitution is one in which an amino acid residue is replaced with an amino acid residue having a similar side chain. Similar amino acids may be included in the following categories: amino acids with basic side chains (e.g., lysine, arginine, histidine); amino acids with acidic side chains (e.g., aspartic acid, glutamic acid); amino acids with uncharged polar side chains (e.g., glycine, asparagine, glutamine, serine, threonine, tyrosine, cysteine, histidine); amino acids with nonpolar side chains (e.g., alanine, valine, leucine, isoleucine, proline, phenylalanine, methionine, tryptophan); amino acids with beta-branched side chains (e.g., threonine, valine, isoleucine), and amino acids with aromatic side chains (e.g., tyrosine, phenylalanine, tryptophan). Proline, which is considered more difficult to classify, shares properties with amino acids that have aliphatic side chains (e.g., leucine, valine, isoleucine, and alanine). In certain circumstances, substitution of glutamine for glutamic acid or asparagine for aspartic acid may be considered a similar substitution in that glutamine and asparagine are amide derivatives of glutamic acid and aspartic acid, respectively. As understood in the art "similarity" between two polypeptides is determined by comparing the amino acid sequence and conserved amino acid substitutes thereto of the polypeptide to the sequence of a second polypeptide (e.g., using GENEWORKS, Align, the BLAST algorithm, or other algorithms described herein and practiced in the art).

As described herein for immunogenic peptide fragments of CCNA1, assays for assessing whether a respective variant folds into a conformation comparable to the non-variant polypeptide or fragment include, for example, the ability of the protein to react with mono- or polyclonal antibodies that are specific for native or unfolded epitopes, the retention of ligand-binding functions, and the sensitivity or resistance of the mutant protein to digestion with proteases (see Sambrook et al., supra). Such variants can be identified, characterized, and/or made according to methods described herein or other methods known in the art, which are routinely practiced by persons skilled in the art.

Isolated/recombinant immunogens included in the immunogenic compositions described herein may be produced and prepared according to various methods and techniques routinely practiced in the molecular biology and/or polypeptide purification arts. Construction of an expression vector that is used for recombinantly producing an immunogen of interest can be accomplished using any of numerous suitable molecular biology engineering techniques known in the art, including, without limitation, the standard techniques of restriction endonuclease digestion, ligation, transformation, plasmid purification, and DNA sequencing, for example as described in Sambrook et al. (1989 and 2001 editions; *Molecular Cloning: A Laboratory Manual*, Cold Spring Harbor Laboratory Press, NY) and Ausubel et al. (Current Protocols in Molecular Biology (2003)). To obtain efficient transcription and translation, the polynucleotide sequence in each recombinant expression construct includes at least one appropriate expression control sequence (also called a regulatory sequence), such as a leader sequence and particularly a promoter operably (i.e., operatively) linked to the nucleotide sequence encoding the immunogen.

Methods that may be used for isolating and purifying a recombinantly produced immunogenic peptide, by way of example, may include obtaining supernatants from suitable host cell/vector systems that secrete the recombinant immunogen into culture media and then concentrating the media using a commercially available filter. Following concentration, the concentrate may be applied to a single suitable purification matrix or to a series of suitable matrices, such as an affinity matrix or an ion exchange resin. One or more reverse phase HPLC steps may be employed to further purify a recombinant polypeptide. These purification methods may also be employed when isolating an immunogen from its natural environment. Methods for large scale production of one or more of the isolated/recombinant immunogens described herein include batch cell culture, which is monitored and controlled to maintain appropriate culture conditions. Purification of the immunogen may be performed according to methods described herein and known in the art and that comport with laws and guidelines of domestic and foreign regulatory agencies.

The presence of a malignant condition in a subject refers to the presence of dysplastic, cancerous and/or transformed cells in the subject, including, for example neoplastic, tumor, non-contact inhibited or oncogenically transformed cells, or the like (e.g., hematologic cancers including lymphomas and leukemias, such as acute myeloid leukemia, chronic myeloid leukemia, etc.) which are known to the art and for which criteria for diagnosis and classification are established (e.g., Hanahan and Weinberg, 2011 *Cell* 144:646; Hanahan and Weinberg 2000 *Cell* 100:57; Cavallo et al., 2011 *Canc. Immunol. Immunother.* 60:319; Kyrigideis et al., 2010 *J. Carcinog.* 9:3). In preferred embodiments contemplated by the present invention, for example, such cancer cells may be cells of acute myeloid leukemia, B-cell lymphoblastic leukemia, T-cell lymphoblastic leukemia, or myeloma, including cancer stem cells that are capable of initiating and serially transplanting any of these types of cancer (see, e.g., see Park et al. 2009 *Molec. Therap.* 17:219).

The CCNA1-derived polypeptides that contain epitopes recognized by and immunogenic for T-cells, as described herein (e.g., SEQ ID NOS:1-8, and variants thereof), may be functionally characterized according to any of a large number of art accepted methodologies for assaying T-cell activity, including determination of T-cell activation or induction and also including determination of T-cell responses that are antigen-specific. Examples include determination of T-cell proliferation, T-cell cytokine release, antigen-specific T-cell stimulation, MHC-restricted T-cell stimulation, CTL activity (e.g., by detecting $^{51}$Cr release from pre-loaded target cells and/or by caspase-3 assay (e.g., Jerome et al. 2003 *Apoptosis* 8:563; He et al., 2005 *J. Imm. Meth.* 304:43), changes in T-cell phenotypic marker expression, and other measures of T-cell functions. Procedures for performing these and similar assays are may be found, for example, in Lefkovits (*Immunology Methods Manual: The Comprehensive Sourcebook of Techniques*, 1998). See also *Current Protocols in Immunology*; Weir, *Handbook of Experimental Immunology*, Blackwell Scientific, Boston, Mass. (1986); Mishell and Shigii (eds.) *Selected Methods in Cellular Immunology*, Freeman Publishing, San Francisco, Calif. (1979); Green and Reed, *Science* 281:1309 (1998) and references cited therein).

Levels of cytokines may be determined according to methods described herein and practiced in the art, including for example, ELISA, ELISPOT, intracellular cytokine staining, and flow cytometry and combinations thereof (e.g., intracellular cytokine staining and flow cytometry). Immune cell proliferation and clonal expansion resulting from an antigen-specific elicitation or stimulation of an immune response may be determined by isolating lymphocytes, such as circulating lymphocytes in samples of peripheral blood cells or cells from lymph nodes, stimulating the cells with antigen, and measuring cytokine production, cell proliferation and/or cell viability, such as by incorporation of tritiated thymidine or non-radioactive assays, such as MTT assays and the like. The effect of an immunogen described herein on the balance between a Th1 immune response and a Th2 immune response may be examined, for example, by determining levels of Th1 cytokines, such as IFN-γ, IL-12, IL-2, and TNF-6, and Type 2 cytokines, such as IL-4, IL-5, IL-9, IL-10, and IL-13.

The level of a CTL immune response thus may be determined by any one of numerous immunological methods described herein and routinely practiced in the art. The level of a CTL immune response may be determined prior to and following administration of any one of the herein described CCNA1-derived polypeptides that contain epitopes recognized by, and immunogenic for, T-cells (or administration of a composition comprising a polynucleotide encoding such a polypeptide). Cytotoxicity assays for determining CTL activity may be performed using any one of several techniques and methods routinely practiced in the art (see, e.g., Henkart et al., "Cytotoxic T-Lymphocytes" in *Fundamental Immunology*, Paul (ed.) (2003 Lippincott Williams & Wilkins, Philadelphia, Pa.), pages 1127-50, and references cited therein).

A binding partner or an antibody is said to be "immunospecific," "specific for" or to "specifically bind" an immunogen of interest if the antibody reacts at a detectable level with the immunogen or immunogenic fragment thereof, preferably with an affinity constant, $K_a$, of greater than or equal to about $10^4$ M$^{-1}$, or greater than or equal to about $10^5$ M$^{-1}$, greater than or equal to about $10^6$ M$^{-1}$, greater than or equal to about $10^7$ M$^{-1}$, or greater than or equal to $10^8$ M$^{-1}$. Affinity of an antibody for its cognate antigen is also commonly expressed as a dissociation constant $K_D$, and an antibody specifically binds to the immunogen of interest if it binds with a $K_D$ of less than or equal to $10^{-4}$ M, less than or equal to about $10^{-5}$ M, less than or equal to about $10^{-6}$ M, less than or equal to $10^{-7}$ M, or less than or equal to $10^{-8}$ M.

Affinities of binding partners or antibodies can be readily determined using conventional techniques, for example, those described by Scatchard et al. (*Ann. N.Y. Acad. Sci. USA* 51:660 (1949)) and by surface plasmon resonance (SPR; BIACORE™, Biosensor, Piscataway, N.J.). For surface plasmon resonance, target molecules are immobilized on a solid phase and exposed to a binding partner (or ligand) in a mobile phase running along a flow cell. If ligand binding to the immobilized target occurs, the local refractive index changes, leading to a change in SPR angle, which can be monitored in real time by detecting changes in the intensity of the reflected light. The rates of change of the SPR signal can be analyzed to yield apparent rate constants for the association and dissociation phases of the binding reaction. The ratio of these values gives the apparent equilibrium constant (affinity) (see, e.g., Wolff et al., *Cancer Res.* 53:2560-2565 (1993)).

Antigen-specific T-cell responses are typically determined by comparisons of observed T-cell responses according to any of the herein described T-cell functional parameters (e.g., proliferation, cytokine release, CTL activity, altered cell surface marker phenotype, etc.) that may be made between T-cells that are exposed to a cognate antigen in an appropriate context (e.g., the antigen used to prime or activate the T-cells, when presented by immunocompatible antigen-presenting cells) and T-cells from the same source population that are exposed instead to a structurally distinct or irrelevant control antigen. A response to the cognate antigen that is greater, with statistical significance, than the response to the control antigen signifies antigen-specificity.

A biological sample may be obtained from a subject for determining the presence and level of an immune response to an immunogenic CCNA1-derived polypeptide as described herein that contains an epitope recognized by, and immunogenic for, T-cells. A "biological sample" as used herein may be a blood sample (from which serum or plasma may be prepared), biopsy specimen, body fluids (e.g., lung lavage, ascites, mucosal washings, synovial fluid), bone marrow, lymph nodes, tissue explant, organ culture, or any other tissue or cell preparation from the subject or a biological source. Biological samples may also be obtained from the subject prior to receiving any immunogenic composition, which biological sample is useful as a control for establishing baseline (i.e., pre-immunization) data.

With respect to all immunoassays and methods described herein for determining an immune response, a person skilled in the art will also readily appreciate and understand experimental control conditions that are appropriately included when practicing these methods. Concentrations of reaction components, types of buffers, temperature, and time periods sufficient to permit interaction of the reaction components can be determined and/or adjusted according to methods described herein and with which persons skilled in the art are familiar.

As generally referred to in the art, and as used herein, sequence identity and sequence homology may be used interchangeably and generally refer to the percentage of nucleotides or amino acid residues in a candidate sequence that are identical with, respectively, the nucleotides or amino acid residues in a native polynucleotide or polypeptide sequence, after aligning the sequences and introducing gaps, if necessary, to achieve the maximum percent sequence identity, and not considering any conservative substitutions as part of the sequence identity. Preferably, an isolated peptide capable of eliciting an antigen-specific T-cell response to human cyclin A1 (CCNA1) as described herein, or an encoding polynucleotide therefore, according to the embodiments disclosed herein shares at least about 75%, at least about 80%, at least about 85%, at least about 90%, at least about 95%, 96%, 97%, 98%, or 99% of the amino acid residues (or of the nucleotides in a polynucleotide encoding such a CCNA1-derived polypeptide) with the immunogenic peptides disclosed herein as SEQ ID NOS:1-8. Such sequence identity may be determined according to well known sequence analysis algorithms, including those available from the University of Wisonsin Genetics Computer Group (Madison, Wis.), such as FASTA, Gap, Bestfit, BLAST, or others.

It has also been determined according to certain embodiments of the present invention that N-terminus extensions of the CCNA1 T-cell epitope-containing peptides described herein can alter the affinity of the peptide binding to a class I major histocompatibility complex (MHC) antigen in association with which the peptide may be displayed on the surface of an antigen-presenting cell (APC), and/or binding of the peptide to the T-cell receptor of a CCNA1-specific T-cell, while C-terminus extensions may also enhance binding and/or activity of the CCNA1-derived peptides. Accordingly, certain embodiments contemplate the use of one or more of the peptides having amino acid sequences set forth in SEQ ID NOS:1-8, and/or variants of such peptides as described herein, and certain embodiments may additionally or alternatively include the use of polypeptides of no more than 20, 19, 18, 17, 16, 15, 14, 13, 12, 11, 10 or 9 amino acids that include in their sequences any of these peptides. Hence, certain contemplated embodiments relate to CCNA1-derived T-cell immunogenic peptides having amino-terminal and/or carboxy-terminal peptide extensions in addition to the amino acid sequences set forth in SEQ ID NOS:1-8, or variants thereof which, as described herein, may be selected for their ability to elicit an antigen-specific T-cell response to CCNA1, such as a CTL response.

As understood by a person skilled in the medical art, the terms, "treat" and "treatment," refer to medical management of a disease, disorder, or condition of a subject (i.e., patient, host, who may be a human or non-human animal) (see, e.g., Stedman's Medical Dictionary). In general, an appropriate dose and treatment regimen provide one or more of the herein described CCNA1-derived peptide immunogens (e.g., SEQ ID NOS:1-8 and variants thereof), and optionally an adjuvant, in an amount sufficient to provide therapeutic and/or prophylactic benefit. Therapeutic and/or prophylactic benefit resulting from therapeutic treatment and/or prophylactic or preventative methods include, for example an improved clinical outcome, wherein the object is to prevent or retard or otherwise reduce (e.g., decrease in a statistically significant manner relative to an untreated control) an undesired physiological change or disorder, or to prevent or retard or retard or otherwise reduce the expansion or severity of such disease or disorder. Beneficial or desired clinical results from treating a subject include, but are not limited to, abatement, lessening, or alleviation of symptoms that result from or are associated the disease or disorder to be treated; decreased occurrence of symptoms; improved quality of life; longer disease-free status (i.e., decreasing the likelihood or the propensity that a subject will present symptoms on the basis of which a diagnosis of a disease is made); diminishment of extent of disease; stabilized (i.e., not worsening) state of disease; delay or slowing of disease progression; amelioration or palliation of the disease state; and remission (whether partial or total), whether detectable or undetectable; and/or overall survival.

"Treatment" can also mean prolonging survival when compared to expected survival if a subject were not receiving treatment. Subjects in need of the methods and compositions described herein include those who already have the disease or disorder as well as subjects prone to have or at risk of developing the disease or disorder. Subjects in need of prophylactic treatment include subjects in whom the disease, condition, or disorder is to be prevented (i.e., decreasing the likelihood of occurrence or recurrence of the disease or disorder). The clinical benefit provided by the compositions (and preparations comprising the compositions) and methods described herein can be evaluated by design and execution of in vitro assays, preclinical studies, and clinical studies in subjects to whom administration of the compositions is intended to benefit. The design and execution of the appropriate preclinical studies and clinical studies can be readily performed by persons skilled in the relevant art(s).

The isolated CCNA1-derived peptide immunogens (including synthetically or recombinantly produced peptides), or recombinant expression vectors encoding such peptide(s) may be administered to a subject in a pharmaceutically or physiologically acceptable or suitable excipient or carrier. Pharmaceutically acceptable excipients are biologically compatible vehicles, e.g., physiological saline, which are described in greater detail herein, that are suitable for administration to a human or other non-human subject including a non-human mammalian subject.

With respect to administration of a recombinant expression vector, a therapeutically effective amount provides an amount of the polynucleotide which is capable of producing a clincally desirable result (i.e., a sufficient amount of the CCNA1-derived peptide immunogen is expressed to induce or enhance the immune response by T-cells specific for CCNA1 (e.g., cell-mediated response, including a cytotoxic T cell response) in a statistically significant manner) in a treated human or non-human animal. As is well known in the medical arts, the dosage for any one patient depends upon many factors, including the patient's size, weight, body surface area, age, the particular compound to be administered, sex, time and route of administration, general health, and other drugs being administered concurrently. Doses will vary, but a preferred dose for administration of an immunogenic composition comprising a recombinant expression vector is sufficient to provide approximately $10^6$ to $10^{12}$ copies of the vector polynucleotide molecule.

Pharmaceutical compositions, including the CCNA1-specific T-cell immunogenic compositions described herein, may be administered in a manner appropriate to the disease or condition to be treated (or prevented) as determined by persons skilled in the medical art. An appropriate dose and a suitable duration and frequency of administration of the compositions will be determined by such factors as the health condition of the patient, size of the patient (i.e., weight, mass, or body area), the type and severity of the patient's disease, the particular form of the active ingredient, and the method of administration. In general, an appropriate dose and treatment regimen provide the composition(s) in an amount sufficient to provide therapeutic and/or prophylactic benefit (such as described herein, including an improved clinical outcome, such as more frequent complete or partial remissions, or longer disease-free and/or overall survival, or a lessening of symptom severity). For prophylactic use, a dose should be sufficient to prevent, delay the onset of, or diminish the severity of a disease associated with disease or disorder. Prophylactic benefit of the immunogenic compositions administered according to the methods described herein can be determined by performing pre-clinical (including in vitro and in vivo animal studies) and clinical studies and analyzing data obtained therefrom by appropriate statistical, biological, and clinical methods and techniques, all of which can readily be practiced by a person skilled in the art.

In general, the amount of an immunogen, including fusion polypeptides as described herein, present in a dose, or produced in situ by an encoding polynucleotide present in a dose, ranges from about 0.01 μg to about 1000 μg per kg of host. The use of the minimum dosage that is sufficient to provide effective therapy is usually preferred. Patients may generally be monitored for therapeutic or prophylactic effectiveness using assays suitable for the condition being treated or prevented, which assays will be familiar to those having ordinary skill in the art and which are described herein. When administered in a liquid form, suitable dose sizes will vary with the size of the patient, but will typically range from about 1 ml to about 500 ml (comprising from about 0.01 μg to about 1000 μg per kg) for a 10-60 kg subject. Optimal doses may generally be determined using experimental models and/or clinical trials. The optimal dose may depend upon the body mass, body area, weight, or blood volume of the subject. As described herein, the appropriate dose may also depend upon the patient's (e.g., human) condition, that is, stage of the disease, general health status, as well as age, gender, and weight, and other factors familiar to a person skilled in the medical art.

For pharmaceutical compositions comprising a nucleic acid molecule such as the recombinant expression vectors described herein, the nucleic acid molecule may be present within any of a variety of delivery systems known to those of ordinary skill in the art, including nucleic acid, and bacterial, viral and mammalian expression systems such as, for example, vector particles and recombinant expression constructs as provided herein. Techniques for incorporating a polynucleotide (e.g., DNA) into such expression systems are well known to those of ordinary skill in the art. In other certain embodiments, the recombinant expression vector, which is typically DNA, may also be "naked," as described, for example, in Ulmer et al., *Science* 259:1745-49 (1993) and reviewed by Cohen, *Science* 259:1691-92 (1993). The uptake of naked DNA may be increased by coating the DNA onto biodegradable beads, which are efficiently transported into the cells.

Nucleic acid molecules may be delivered into a cell according to any one of several methods described in the art (see, e.g., Akhtar et al., *Trends Cell Bio.* 2:139 (1992); *Delivery Strategies for Antisense Oligonucleotide Therapeutics*, ed. Akhtar, 1995, Maurer et al., *Mol. Membr. Biol.* 16:129-40 (1999); Hofland and Huang, *Handb. Exp. Pharmacol.* 137:165-92 (1999); Lee et al., *ACS Symp. Ser.* 752:184-92 (2000); U.S. Pat. No. 6,395,713; International Patent Application Publication No. WO 94/02595); Selbo et al., *Int. J. Cancer* 87:853-59 (2000); Selbo et al., *Tumour Biol.* 23:103-12 (2002); U.S. Patent Application Publication Nos. 2001/0007666, and 2003/077829). Such delivery methods known to persons having skill in the art, include, but are not restricted to, encapsulation in liposomes, by iontophoresis, or by incorporation into other vehicles, such as biodegradable polymers; hydrogels; cyclodextrins (see, e.g., Gonzalez et al., *Bioconjug. Chem.* 10:1068-74 (1999); Wang et al., International Application Publication Nos. WO 03/47518 and WO 03/46185); poly(lactic-co-glycolic) acid (PLGA) and PLCA microspheres (also useful for delivery of peptides and polypeptides and other substances) (see, e.g., U.S. Pat. No. 6,447,796; U.S. Patent Application Publication No. 2002/130430); biodegradable nanocapsules; and bioadhesive microspheres, or by proteinaceous vectors (International Application Publication No. WO 00/53722). In another embodiment, the nucleic acid molecules can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives (see also, e.g., U.S. Patent Application Publication No. 2003/0077829).

Certain of the presently disclosed invention embodiments include preventative treatment of a subject or cells, tissues or organs of a subject, that is suspected of having or of being susceptible to a condition associated with CCNA1 overexpression. The preventative treatment may be the same as or different from the regimen (dosing and schedule, as well as choice of immunogenic CCNA1-derived peptide and/or other therapeutic agents such as antigen-presenting cells or adoptively transferred T-cells) employed to treat a subject or cells, tissues or organs of a subject that has been confirmed to have a condition associated with CCNA1 overexpression. Prevention and/or treatment may also include the use of vaccines comprising compositions disclosed herein, for example by way of illustration and not limitation, one or more CCNA1-derived peptides that are immunogenic for antigen-specific T-cells.

Particular contemplated embodiments relate to immunotherapeutic regimens using the herein described compositions and methods to elicit T-cell immune responses that are directed against leukemic stem cells (LSC). More particularly, and according to non-limiting theory, as disclosed herein it is believed that by certain of the present embodiments, cytotoxic T lymphocyte (CTL) responses are elicited that are specifically targeted against LSC. These and related embodiments are thus believed to provide a highly specific approach to eliminate or substantially reduce LSC populations in a subject, thereby providing benefits for the treatment of leukemias that are characterized by CCNA1 overexpression, such as acute myeloid leukemia (AML). These approaches also offer unprecedented advantages pertaining to the specificity afforded by the restricted pattern of CCNA1 overexpression, and to the avoidance of undesirable generalized toxic effects that accompany many less target-specific immunotherapeutic approaches.

A condition associated with CCNA1 overexpression includes any disorder or condition in which underactivity, overactivity or improper activity of a CCNA1 cellular or molecular event is present, and typically results from unusually high (with statistical significance) levels of CCNA1 expression on afflicted cells (e.g., leukemic cells such as AML cells or leukemic stem cells), relative to normal cells. A subject having such a disorder or condition would benefit from treatment with a composition or method of the presently described embodiments. Some conditions associated with CCNA1 overexpression thus may include acute as well as chronic disorders and diseases, such as those pathological conditions that predispose the subject to a particular disorder.

Some non-limiting examples of conditions associated with CCNA1 overexpression include hyperproliferative disorders, which refer to states of activated and/or proliferating cells (which may also be transcriptionally overactive) in a subject including tumors, neoplasms, cancer, malignancy, etc. In addition to activated and/or proliferating cells, the hyperproliferative disorder may also include an aberration or dysregulation of cell death processes, whether by necrosis or apoptosis. Such aberration of cell death processes may be associated with a variety of conditions, including cancer (including primary, secondary malignancies as well as metastasis) and other conditions.

According to certain embodiments, virtually any type of cancer that is characterized by CCNA1 overexpression may be treated through the use of compositions and methods disclosed herein, including but not limited to hematological cancers (e.g., leukemia including acute myeloid leukemia (AML), T or B cell lymphomas, myeloma, and others) are considered. Furthermore, "cancer" may refer to any accelerated proliferation of cells, including solid tumors, ascites tumors, blood or lymph or other malignancies; connective tissue malignancies; metastatic disease; minimal residual disease following transplantation of organs or stem cells; multi-drug resistant cancers, primary or secondary malignancies, angiogenesis related to malignancy, or other forms of cancer. Also contemplated within the presently disclosed embodiments are specific embodiments wherein only one of the above types of disease is included, or where specific conditions may be excluded regardless of whether or not they are characterized by CCNA1 overexpression.

Certain methods of treatment or prevention contemplated herein include administering a composition that comprises a desired nucleic acid molecule such that it stably integrates into the chromosome of certain desired cells. For example, such compositions may be integrated into immune system cells (e.g., antigen-presenting cells and/or T-cells) in order to promote a desired, CCNA1-targeted T-cell response.

As used herein, administration of a composition or therapy refers to delivering the same to a subject, regardless of the route or mode of delivery. Administration may be effected continuously or intermittently, systemically or locally. Administration may be for treating a subject already confirmed of having a recognized condition, disease or disease state, or for subjects susceptible to or at risk of developing such a condition, disease or disease state. Co-administration may include simultaneous and/or sequential delivery of multiple agents in any order and on any dosing schedule.

An effective amount of a therapeutic or pharmaceutical composition refers to an amount sufficient, at dosages and for periods of time needed, to achieve the desired clinical results or beneficial treatment, as described herein. An effective amount may be delivered in one or more administrations. If the administration is to a subject already known or confirmed to have a disease or disease-state, the term "therapeutic amount" may be used in reference to treatment, whereas "prophylactically effective amount" may be used to describe administrating an effective amount to a subject that is susceptible or at risk of developing a disease or disease-state as a preventative course.

Pharmaceutical Compositions

In certain embodiments of the disclosed invention, a pharmaceutical composition comprising at least one herein disclosed composition (e.g., an isolated peptide capable of eliciting an antigen-specific T-cell response to human cyclin A1, or a recombinant expression vector encoding the same), is administered to a subject. As used herein, a pharmaceutical composition generally refers to the combination of an active pharmaceutical drug or other therapeutic agent and an excipient or carrier, whether inert or active, wherein the pharmaceutical composition comprises at least one isolated peptide capable of eliciting an antigen-specific T-cell response to CCNA1 (or a recombinant expression vector encoding the same) that is suitable for therapeutic use, including prophylactic use, in vivo, in vitro, or ex vivo.

In certain embodiments, the present invention relates to formulations of one or more compositions disclosed herein in pharmaceutically-acceptable excipients or carriers for administration to a cell or a subject either alone, or in combination, with one or more other modalities of therapy. It is understood that, if desired, a composition as disclosed herein may be administered in combination with other agents as well, including therapeutic agents. Such compositions may be synthesized de novo or purified from host cells or other biological sources.

It will be apparent that any of the pharmaceutical compositions described herein can contain pharmaceutically acceptable excipients or other carriers, and may contain acceptable salts. Such salts can be prepared, for example, from pharmaceutically acceptable non-toxic bases, including organic bases (e.g. salts of primary, secondary and tertiary amines and basic amino acids) and inorganic bases (e.g. sodium, potassium, lithium, ammonium, calcium and magnesium salts).

While any suitable carrier known to those of ordinary skill in the art may be employed in the pharmaceutical compositions as described herein (e.g., pharmaceutical compositions that comprise the presently disclosed isolated peptide capable of eliciting a CCNA1-specific T-cell response, or a recombinant expression vector encoding the same) the type of carrier will typically vary depending on the mode of administration. Compositions of the present invention may in certain embodiments be formulated for any appropriate manner of administration, including for example, topical, oral, nasal, mucosal, intravenous, intratumor, rectal, parenteral, intraperitoneal, subcutaneous and intramuscular administration.

Carriers for use with such pharmaceutical compositions are biocompatible, and may also be biodegradable. In certain embodiments, the formulation preferably provides a relatively constant level of active component release. In other embodiments, however, a more rapid rate of release immediately upon administration may be desired. The formulation of such compositions is well within the level of ordinary skill in the art using known techniques. Illustrative carriers useful in this regard include microparticles of poly(lactide-co-glycolide), polyacrylate, latex, starch, cellulose, dextran and the like. Other illustrative delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active compound contained within a sustained release formulation depends upon the route of administration, the rate and expected duration of release and the nature of the condition to be treated or prevented.

Certain embodiments of the invention may utilize an alkalinizing agent, which is typically soluble in aqueous phase under physiological pH conditions. Such alkalinizing agents are well known to those in the art and may include alkali or alkaline-earth metal hydroxides, carbonates, bicarbonates, phosphates, sodium borate, as well as basic salts (as discussed herein).

In another illustrative embodiment, biodegradable microspheres (e.g., polylactate polyglycolate) are employed as carriers for the compositions that are herein disclosed. Suitable biodegradable microspheres are disclosed, for example, in U.S. Pat. Nos. 4,897,268; 5,075,109; 5,928,647; 5,811,128; 5,820,883; 5,853,763; 5,814,344, 5,407,609 and 5,942,252. Another illustrative carrier/delivery system employs a carrier comprising particulate-protein complexes, such as those described in U.S. Pat. No. 5,928,647, which are capable of inducing a class I-restricted cytotoxic T lymphocyte response in a host.

In another illustrative embodiment, calcium phosphate core particles are employed as carriers, adjuvants, or as controlled release matrices for the compositions of this invention. In certain embodiments, an adjuvant may be necessary in order to increase the immune response of the subject. Adjuvants are well known in the art and may include cytokines, dead viruses or bacteria or fragments thereof, antibodies, or any other agent that heightens an immune response.

The pharmaceutical compositions as provided herein will often further comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions described herein may be formulated as lyophilizates.

The pharmaceutical compositions described herein may be presented in unit-dose or multi-dose containers, such as sealed ampoules or vials. Such containers are typically sealed in such a way to preserve the sterility and stability of the formulation until use. In general, formulations may be stored as suspensions, solutions or emulsions in oily or aqueous vehicles. Alternatively, a pharmaceutical composition may be stored in a freeze-dried condition requiring only the addition of a sterile liquid carrier immediately prior to use.

The development of suitable dosing and treatment regimens for using the particular compositions described herein in a variety of treatment regimens, including e.g., oral, parenteral, intravenous, intranasal, and intramuscular administration and formulation, is well known in the art, some of which are briefly discussed below for general purposes of illustration.

In certain applications, the pharmaceutical compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet. The pharmaceutical composition may take the form of tablets, lozenges, pills, troches, capsules, elixirs, powders, granules, suspensions, emulsions, syrups, or tinctures. Slow-release or delayed-release forms may also be prepared (for example, in the form of coated particles, multi-layer tablets or microgranules).

The compositions may also contain any of a variety of additional components, for example, pharmaceutically acceptable binders, such as gum tragacanth, gum acacia, sodium alginate, carboxymethylcellulose, polyethylene glycol, cornstarch, or gelatin; excipients, such as dicalcium phosphate; a disintegrating agent, such as corn starch, potato starch, methylcellulose, polyvinylpyrrolidone, xanthan gum, bentonite, agar, alginic acid and the like; a lubricant, such as magnesium stearate; a sweetening agent, such as sucrose, lactose, glucose, aspartame or saccharin may be added; a diluent, such as lactose, sorbitol, mannitol, dextrose, kaolin, cellulose, calcium carbonate, calcium silicate or dicalcium phosphate; a flavoring agent, such as peppermint, oil of wintergreen, orange, raspberry, bubblegum, or cherry flavoring, coating agents, such as polymers or copolymers of acrylic acid and/or methacrylic acid and/or their esters, waxes, fatty alcohols, zein, shellac or gluten; preservatives, such as sodium benzoate, vitamin E, alpha-tocopherol, ascorbic acid, methyl paraben, propyl paraben, or sodium bisulphate; lubricants, such as magnesium stearate, stearic acid, sodium oleate, sodium chloride or talc; and/or time delay agents, such as glyceryl monostearate or glyceryl distearate.

In certain embodiments, a tablet or pill may be in the form of a compression coating or alternatively in the form of a spray coating. A compression coating may include a small tablet or pill utilized as part of the compression of a second tablet and wherein the small tablet is located nearly in the center of the rest of the powder compressed outside. A spray coating may include an overcoating of a tablet with the coating preparation containing an active substance.

In certain embodiments, the pharmaceutical compositions of the present invention include "slow-release" or "immediate release" forms. As used herein, "slow-release" generally refers to a release of 20% to 60% in 1 hour and greater than 70% in 6 hours or 40% to 80% in 2 hours, and greater than 70% in 6 hours in 500 ml of water (HCl 0.1N) in USP apparatus 1 (37° C., 100 RPM). Whereas, "immediate release" generally refers to a release of more than 70% in 30 minutes, in 500 ml of water (HCl 0.1N) in USP apparatus 1 (37° C., 100 RPM).

In certain embodiments, the tablet or pill weighs in the range of 100 mg, 200 mg, 300 mg, 400 mg, 500 mg, 600 mg, 700 mg, 800 mg, and any value therebetween or greater. The oral dosage formulations of certain embodiments of the present invention may be manufactured according to known methods in the art, and may be packaged as known, including in a moisture and/or oxygen and/or light protective packaging material.

In addition, liquid forms of the pharmaceutical compositions may include a liquid carrier, such as water, oils (olive oil, peanut oil, sesame oil, sunflower oil, safflower oil, arachis oil, coconut oil), liquid paraffin, ethylene glycol, propylene glycol, polyethylene glycol, ethanol, propanol, isopropanol, glycerol, fatty alcohols, triglycerides, or mixtures thereof.

If the subject composition is administered parenterally, the composition may also include sterile aqueous or oleaginous solution or suspension. Suitable non-toxic parenterally acceptable diluents or solvents include water, Ringer's solution, isotonic salt solution, 1,3-butanediol, ethanol, propylene glycol or polythethylene glycols in mixtures with water. Aqueous solutions or suspensions may further comprise one or more buffering agents, such as sodium acetate, sodium citrate, sodium borate or sodium tartrate. Of course, any material used in preparing any dosage unit formulation should be pharmaceutically pure and substantially non-toxic in the amounts employed. In addition, the active compounds may be incorporated into sustained-release preparation and formulations. Dosage unit form, as used herein, refers to physically discrete units suited as unitary dosages for the subject to be treated; each unit may contain a predetermined quantity of active compound calculated to produce the desired therapeutic effect in association with the required pharmaceutical carrier. The specification for the dosage unit forms are largely dictated by and directly dependent on the unique characteristics of the active compound and the particular therapeutic or prophylactic effect to be achieved, as well as the limitations inherent in the art of compounding such an active compound for treatment in subjects. Exemplary and non-limiting dosage ranges may be from 0.1-10 mg/kg, 1.0-20 mg/kg, 5.0-50 mg/kg, 10-100 mg/kg, or any values therebetween.

Typically, these formulations will contain at least about 0.01% of the active compound or more by weight of the active substance. However, the percentage of the active ingredient(s) may be varied and may conveniently be between about 1-99%, including about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In certain circumstances it will be desirable to deliver the pharmaceutical compositions disclosed herein topically, orally, subcutaneously, parenterally, intravenously, intra-muscularly, or even intraperitoneally. Such approaches are well known to the skilled artisan, some of which are further described, for example, in U.S. Pat. No. 5,543,158; U.S. Pat. No. 5,641,515 and U.S. Pat. No. 5,399,363. In certain embodiments, solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations generally will contain a preservative to prevent the growth of microorganisms.

In one embodiment, for parenteral administration in an aqueous solution, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "*Remington's Pharmaceutical Sciences*" 15th Edition, pages 1035-1038 and 1570-1580). Some variation in dosage will necessarily occur depending on the condition of the subject being treated. Moreover, for human administration, preparations preferably meet sterility, pyrogenicity, and the general safety and purity standards as required by FDA Office of Biologics standards.

In another embodiment of the invention, the compositions disclosed herein may be formulated in a neutral or salt form. Illustrative pharmaceutically-acceptable salts include the acid addition salts (formed with the free amino groups of the protein) which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective.

The carriers can further comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" refers to molecular entities and compositions that do not produce an allergic or similar untoward reaction when administered to a human.

In certain embodiments, the pharmaceutical compositions may be delivered by intranasal sprays, inhalation, and/or other aerosol delivery vehicles. Methods for delivering genes, nucleic acids, and peptide compositions directly to the lungs via nasal aerosol sprays have been described, e.g., in U.S. Pat. No. 5,756,353 and U.S. Pat. No. 5,804,212. Likewise, the delivery of drugs using intranasal microparticle resins (Takenaga et al., *J Controlled Release* 1998 Mar. 2; 52(1-2):81-7) and lysophosphatidyl-glycerol compounds (U.S. Pat. No. 5,725,871) are also well-known in the pharmaceutical arts. An illustrative example of transmucosal drug delivery in the form of a polytetrafluoroetheylene support matrix is described in U.S. Pat. No. 5,780,045.

In certain embodiments, liposomes, nanocapsules, microparticles, microencapsulation, lipid particles, vesicles, and the like, are used for the introduction of the presently disclosed compositions into suitable host cells/organisms. In particular, such compositions may be formulated for delivery either encapsulated in a lipid particle, a liposome, a vesicle, a nanosphere, microsphere or microparticle, a nanoparticle or the like. Alternatively, compositions disclosed herein can be bound, either covalently or non-covalently, to the surface of such carrier vehicles.

The formation and use of liposome and liposome-like preparations as potential drug carriers is generally known to those of skill in the art. Liposomes have been used successfully with a number of cell types that are normally difficult to transfect by other procedures, including T-cell suspensions, primary hepatocyte cultures and PC 12 cells (Renneisen et al., *J Biol Chem.* 1990 Sep. 25; 265(27):16337-42; Muller et al., *DNA Cell Biol.* 1990 April; 9(3):221-9). In addition, liposomes are free of the DNA length constraints that are typical of viral-based delivery systems. Liposomes have been used effectively to introduce genes, various drugs, radiotherapeutic agents, enzymes, viruses, transcription factors, allosteric effectors and the like, into a variety of cultured cell lines and animals. Furthermore, the use of liposomes does not appear to be associated with autoimmune responses or unacceptable toxicity after systemic delivery.

In certain embodiments, liposomes are formed from phospholipids that are dispersed in an aqueous medium and spontaneously form multilamellar concentric bilayer vesicles (also termed multilamellar vesicles (MLVs).

Alternatively, in other embodiments, the invention provides for pharmaceutically-acceptable nanocapsule formulations of the compositions of the present invention. Nanocapsules can generally entrap compounds in a stable and reproducible way. To avoid side effects due to intracellular polymeric overloading, such ultrafine particles (sized around 0.1 μm) may be designed using polymers able to be degraded in vivo. Such particles can be made as described, for example, by Couvreur et al., *Crit Rev Ther Drug Carrier Syst.* 1988; 5(1):1-20; zur Muhlen et al., *Eur J Pharm Biopharm.* 1998 March; 45(2):149-55; Zambaux et al. *J Controlled Release* 1998 Jan. 2; 50(1-3):31-40; and U.S. Pat. No. 5,145,684.

Dosing Schedules

Routes and frequency of administration of the therapeutic compositions described herein, as well as dosage, will vary from individual to individual, and may be readily established using standard techniques. In general, the pharmaceutical compositions may be administered by injection (e.g., intracutaneous, intramuscular, intravenous or subcutaneous), intranasally (e.g., by aspiration) or orally. Suitable dosage formulations and methods of administering the agents are readily determined by those of skill in the art. In certain instances, the isolated peptide capable of eliciting a CCNA1-specific T-cell response to human cyclin A1 (or a recombinant expression vector encoding the same) may be administered at about 1 mg/kg, 5 mg/kg, 10 mg/kg, 20 mg/kg, 25 mg/kg, 30 mg/kg, 35 mg/kg 40 mg/kg, 45 mg/kg, 50 mg/kg, 60 mg/kg, 70 mg/kg, 75 mg/kg, 80 mg/kg, 90 mg/kg, 100 mg/kg, 125 mg/kg, 150 mg/kg, 175 mg/kg, 200 mg/kg or any value therebetween or greater. In certain instances, doses (and optionally, at least one other therapeutic agent dose) may be provided between 1 day and 14 days over a 30 day period. In certain instances, doses (and optionally, at least one other therapeutic agent dose) may be provided 1, 2, 3, 4, 5, 6, 7, 8, 9, 10, 11, 12, 13, or 14 days over a 60 day period. Alternate protocols may be appropriate for individual subjects. A suitable dose is an amount of a compound that, when administered as described above, is capable of altering or ameliorating symptoms, or is at least 10-50% above the basal (i.e., untreated) level, which can be monitored by measuring specific levels of blood components, for example, detectable levels of circulating leukemic cells.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated subjects as compared to non-treated subjects. Increases in preexisting immune responses to a tumor protein generally correlate with an improved clinical outcome. Such immune responses may generally be evaluated using standard proliferation, cytotoxicity or cytokine assays, which are routine in the art and may be performed using samples obtained from a subject before and after treatment.

Standard techniques may be used for recombinant DNA, peptide and oligonucleotide synthesis, immunoassays and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references in microbiology, molecular biology, biochemistry, molecular genetics, cell biology, virology and immunology techniques that are cited and discussed throughout the present specification. See, e.g., Sambrook, et al., *Molecular Cloning: A Laboratory Manual,* 3d ed., Cold Spring Harbor Laboratory Press, Cold Spring Harbor, N.Y.; *Current Protocols in Molecular Biology* (John Wiley and Sons, updated July 2008); *Short Protocols in Molecular Biology: A Compendium of Methods from Current Protocols in Molecular Biology,* Greene Pub. Associates and Wiley-Interscience; Glover, *DNA Cloning: A Practical Approach,* vol. I & II (IRL Press, Oxford Univ. Press USA, 1985); *Current Protocols in Immunology* (Edited by: John E. Coligan, Ada M. Kruisbeek, David H. Margulies, Ethan M. Shevach, Warren Strober 2001 John Wiley & Sons, NY, NY); *Real-Time PCR: Current Technology and Applications,* Edited by Julie Logan, Kirstin Edwards and Nick Saunders, 2009, Caister Academic Press, Norfolk, UK; Anand, *Techniques for the Analysis of Complex Genomes,* (Academic Press, New York, 1992); Guthrie and Fink, *Guide to Yeast Genetics and Molecular Biology* (Academic Press, New York, 1991); *Oligonucleotide Synthesis* (N. Gait, Ed., 1984); *Nucleic Acid Hybridization* (B. Hames & S. Higgins, Eds., 1985); *Transcription and Translation* (B. Hames & S. Higgins, Eds., 1984); *Animal Cell Culture* (R. Freshney, Ed., 1986); Perbal, *A Practical Guide to Molecular Cloning* (1984); *Next-Generation Genome Sequencing* (Janitz, 2008 Wiley-VCH); *PCR Protocols (Methods in Molecular Biology)* (Park, Ed., 3$^{rd}$ Edition, 2010 Humana Press); *Immobilized Cells And Enzymes* (IRL Press, 1986); the treatise, Methods In Enzymology (Academic Press, Inc., N.Y.); *Gene Transfer Vectors For Mammalian Cells* (J. H. Miller and M. P. Calos eds., 1987, Cold Spring Harbor Laboratory); Harlow and Lane, *Antibodies,* (Cold Spring Harbor Laboratory Press, Cold Spring Harbor, N.Y., 1998); *Immunochemical Methods In Cell And Molecular Biology* (Mayer and Walker, eds., Academic Press, London, 1987); *Handbook Of Experimental Immunology*, Volumes I-IV (D. M. Weir and CC Blackwell, eds., 1986); Roitt, *Essential Immunology*, 6th Edition, (Blackwell Scientific Publications, Oxford, 1988); *Embryonic Stem Cells: Methods and Protocols* (Methods in Molecular Biology) (Kurstad Turksen, Ed., 2002); *Embryonic Stem Cell Protocols: Volume I: Isolation and Characterization* (Methods in Molecular Biology) (Kurstad Turksen, Ed., 2006); *Embryonic Stem Cell Protocols: Volume II: Differentiation Models* (Methods in Molecular Biology) (Kurstad Turksen, Ed., 2006); *Human Embryonic Stem Cell Protocols* (Methods in Molecular Biology) (Kursad Turksen Ed., 2006); *Mesenchymal Stem Cells: Methods and Protocols* (Methods in Molecular Biology) (Darwin J. Prockop, Donald G. Phinney, and Bruce A. Bunnell Eds., 2008); *Hematopoietic Stem Cell Protocols* (Methods in Molecular Medicine) (Christopher A. Klug, and Craig T. Jordan Eds., 2001); *Hematopoietic Stem Cell Protocols* (Methods in Molecular Biology) (Kevin D. Bunting Ed., 2008) *Neural Stem Cells: Methods and Protocols* (Methods in Molecular Biology) (Leslie P. Weiner Ed., 2008).

Unless specific definitions are provided, the nomenclature utilized in connection with, and the laboratory procedures and techniques of, molecular biology, analytical chemistry, synthetic organic chemistry, and medicinal and pharmaceutical chemistry described herein are those well known and commonly used in the art. Standard techniques may be used for recombinant technology, molecular biological, microbiological, chemical syntheses, chemical analyses, pharmaceutical preparation, formulation, and delivery, and treatment of patients.

Each embodiment described in this specification is to be applied mutatis mutandis to every other embodiment unless expressly stated otherwise.

Unless the context requires otherwise, throughout the present specification and claims, the word "comprise" and variations thereof, such as, "comprises" and "comprising" are to be construed in an open, inclusive sense, that is, as "including, but not limited to". By "consisting of" is meant including, and typically limited to, whatever follows the phrase "consisting of." By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are required and may or may not be present depending upon whether or not they affect the activity or action of the listed elements.

In this specification and the appended claims, the singular forms "a," "an" and "the" include plural references unless the content clearly dictates otherwise. As used herein, in particular embodiments, the terms "about" or "approximately" when preceding a numerical value indicates the value plus or minus a range of 5%, 6%, 7%, 8% or 9%. In other embodiments, the terms "about" or "approximately" when preceding a numerical value indicates the value plus or minus a range of 10%, 11%, 12%, 13% or 14%. In yet other embodiments, the terms "about" or "approximately" when preceding a numerical value indicates the value plus or minus a range of 15%, 16%, 17%, 18%, 19% or 20%.

Reference throughout this specification to "one embodiment" or "an embodiment" or "an aspect" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. When steps of a method are described or claimed, and the steps are described as occurring in a particular order, the description of a first step occurring (or being performed) "prior to" (i.e., before) a second step has the same meaning if rewritten to state that the second step occurs (or is performed) "subsequent" to the first step.

The following Examples are presented by way of illustration and not limitation.

EXAMPLES

Example 1

Identification of Human Cyclin A1 (CCNA1) as an Immunotherapeutic Target for Leukemia and Characterization of CCNA1 T-Cell Immunogenic Epitopes In this Example, analyses of differential gene expression were performed to identify cyclin A1 (CCNA1), an intracellular protein, as a candidate new T-cell target protein. By way of brief background, CCNA1 was reported to regulate the progression of male germ cells through meiosis I and was therefore selectively expressed in testis (Yang et al., 1997 *Cancer Res* 57 (5):913-920; Wolgemuth et al., 2004 *Int J Androl* 27 (4):192-199. doi:10.1111/j.1365-2605.2004.00480.x IJA480 [pii]). Published reports have shown that CCNA1−/− mice were viable, and were phenotypically normal with the exception of male infertility (Krug et al., 2009 *Int J Oncol* 34 (1):129-136; Nickerson et al., 2007 *Dev Biol* 306 (2):725-735. doi:S0012-1606 (07) 00783-X [pii] 10.1016/j.ydbio. 2007.04.009). CCNA1 was also shown to be aberrantly expressed in AML as well as other malignancies (Yang et al., 1997 *Cancer Res* 57 (5): 913-920; Stirewalt et al., 2008 *Genes Chromosomes Cancer* 47 (1):8-20. doi:10.1002/gcc.20500). In AML, CCNA1 sustained the malignant phenotype through pro-proliferative and anti-apoptotic activities (Chan et al., 2009 *Oncogene* 28 (43):3825-3836. doi: one 2009236 [pii] 10.1038/ onc.2009.236; Jang et al., 2008 *Cancer Res* 68 (12):4559-4570. doi: 68/12/4559 [pii] 10.1158/0008-5472.CAN-08-0021; Ji et al., 2007 *Int J Cancer* 121 (4):706-713. doi: 10.1002/ijc. 22634), and over-expression of CCNA1 in mice caused dysplastic myelopoiesis and transplantable myeloid leukemias in 15% of the mice (Liao et al., 2001 *Proc Natl Acad Sci USA* 98 (12):6853-6858. doi:10.1073/pnas.12154 0098 12154 0098 [pii]).

Here, CCNA1 is shown to act as a testis-leukemia-antigen harboring a multitude of potentially immunogenic MHC class I epitopes that can be used to generate CD8+ T-cells from healthy donors. T-cells so generated were able to recognize and lyse leukemic cells.

Material and Methods

Human Samples.

For quantitative realtime PCR (qRT PCR), mononuclear cells of AML patients from peripheral blood and bone marrow (BM), BM mononuclear cells from chronic myeloid leukemia (CIVIL) patients and patients with myelodysplastic syndrome (MDS), and GM-CSF-mobilized CD34+ cells were isolated by leukopheresis or FICOLL-HYPAQUE™ neutral, highly branched, high-mass, hydrophilic polysaccharide (Biochrom, Cambrige, UK). All AML samples contained more than 60% malignant cells (average 84%). Cells were collected at Fred Hutchinson Cancer Research Center (FHCRC), Seattle, Wash., USA, and at Charité Campus Benjamin Franklin, Berlin, Germany. For the generation of T-cell lines, leukopheresis products were obtained from two healthy donors at the FHCRC, Seattle. All samples were collected after written informed consent and with approval of the institutional review boards of the respective institutions.

Cell Lines.

Epstein-Barr virus (EBV) transformed lymphoblastoid cell lines (LCLs) were generated as described (Riddell et al., 1991 *J Immunol* 146 (8):2795-2804). TM-LCL were used as feeder cells in the Rapid Expansion Protocol (REP) (Ho et al., 2006 *J Immunol Methods* 310 (1-2):40-52. doi: S0022-1759 (05) 00429-1 [pii] 10.1016/j.jim.2005. 11.023). The T-cell/B-cell hybrid cell line T2 used for presentation of epitopes expressed only HLA A*0201, but was TAP deficient. LCL 721.221 expressed no HLA class I due to a radiation induced deletion of the relevant alleles, and was stably transduced with the retroviral vector pLBPC containing HLA A*0201 (Akatsuka et al., 2002 *Tissue Antigens* 59 (6):502-511. doi: tan 590607 [pii]). LCLs and T2 cells were maintained as described (Ho et al., 2006 *J Immunol Methods* 310 (1-2):40-52. doi: S0022-1759 (05) 00429-1 [pii] 10.1016/j.jim.2005. 11.023). Cell lines K562 (CML), THP-1, HL60, KG1 (AML) and U937 (monocytic cell line) were maintained in RPMI 1640 supplemented with 100 U/ml penicillin, 100 g/ml streptomycin (Invitrogen, Carlsbad, Calif.), and 10% fetal bovine serum (FBS), and for THP-1, 50 M β-mercaptoethanol (Sigma, St. Louis, Mo.) was also added. CTLs and dendritic cells (DCs) were maintained as described (Ho et al., 2006 *J Immunol Methods* 310 (1-2): 40-52).

Microarray Data Analysis.

Two panels of microarray data sets (Affymetrix, Santa Clara, Calif.) were used in this study: (1) nine AML LSC samples (Lineage–, CD34+, CD38–, CD90, (Majeti et al., 2009 *Proc Natl Acad Sci USA* 106 (9):3396-3401), seven corresponding leukemic blast samples (Lineage, CD34), four HSC samples (Lineage, CD34+, CD38–, CD90+(Majeti et al., 2009 *Proc Natl Acad Sci USA* 106 (9):3396-3401)) and data sets of peripheral blood mononuclear cells (PBMCs), CD34+ BM mononuclear cells and tissues (NCBI GEO server GSM279585-279588, 414970, 414972, 414975, 419165-419174, 457175-457177, 483480-483496, 80576, 80582, 80602, 80615, 80619, 80653, 80689, 80712, 80734, 80738, 80739, 80759, 80792, 80824, 80826, 80867, 80869, HG U133 plus 2.0 format); and (2) 30 samples of AML cells (>75% malignant cells, Stirewalt et al., 2008 *Genes Chromosomes Cancer* 47 (1):8-20; and unpublished) and 58 tissue samples (NCBI GEO server GSM18873, 18874, 18881, 18882, 18899-18906, 18909, 18910, 18917, 18918, 18921, 18922, 18943-18962, 18965, 18966, 18969-18974, 18977, 18978, 18981, 18982, 18995-18998, 19001, 19002, 19013, 19014, 44671-44693, 44699-44706, HG U133A format). Samples were normalized using the invariant set method (dChip 2.0 software, Li et al., 2001 *Proc Natl Acad Sci USA* 98 (1):31-36). Before analyzing the panels at a single-probe-set level, unsupervised hierarchical clustering was performed to rule out clustering in accordance to the origin of the samples rather than of the biological background of the data sets. Expression values of probe set 205899_at in LSCs were compared with other cell types using a two-tailed Mann-Whitney test. CCNA1 expression values of seven paired samples of LSC and the corresponding leukemic blasts (Lineage–, CD34–) were compared using a two-tailed Wilcoxon Signed Rank test.

Quantitative Realtime PCR.

Total RNA was extracted using TRIZOL™ guanidinium thiocyanate-phenol-chloroform reagent (Invitrogen) or RNAEASY™ nucleic acid isolation Mini Kit (Qiagen, Hilden, Germany). Reverse transcription was performed using SUPERSCRIPT™ III reverse transcription reagent (Invitrogen) or OMNISCRIPT™ reverse transcription reagent (Qiagen). A panel of cDNAs from pooled healthy tissues was purchased from Clontech (Mountain View, Calif.), and five samples of healthy BM were purchased from Cambrex (Rutherford, N.J.). Quantitative two-step RT PCR was performed on an ABI 7500 machine (Applied Biosystems, Carlsbad, Calif.) with TA=60° C. using the following primers and probes:

Glyceraldehyde 3-phosphate dehydrogenase (GAPDH)_fwd:

[SEQ ID NO: 11]
GAG TCA ACG GAT TTG GTC GT;

GAPDH_probe, labeled with 6FAM (6-carboxyfluorescein) at the 5' end and TAMRA (carboxytetramethylrhodamine) at the 3' end:

[SEQ ID NO: 12]
GAT ATT GTT GCC ATC AAT GAC CCC T;

GAPDH_rev:

[SEQ ID NO: 13]
GAC AAG CTT CCC GTT CTC AG;

CCNA1_fwd:

[SEQ ID NO: 14]
CAT GAA GAA GCA GCC AGA CA;

CCNA1_probe, labeled with 6FAM (6-carboxyfluorescein) at the 5' end and TAMRA (carboxytetramethylrhodamine) at the 3' end:

[SEQ ID NO: 15]
TTC GAG CAG AGA CCC TGT ATC TGG;

CCNA1_rev:

[SEQ ID NO: 16]
TTC GAA GCC AAA AGC ATA GC.

Crossing points were plotted against standard curves of pCR4-TOPO plasmids (Invitrogen) containing the respective PCR product as described (Keilholz et al., 2004 *Clin Cancer Res* 10 (5):1605-1612). All reactions were performed in duplicate. CCNA1 expression is given as copies per copies of GAPDH.

Cytokines and Peptides.

Recombinant human IL-1, IL-4, IL-7, IL-15, and TNFα were obtained from R&D Systems (Minneapolis, Minn.), IL-2 and GM-CSF from Chiron (Emeryville, Calif.), PGE2 from MP Biomedicals (Irvine, Calif.), and IL-21 from Peprotech (Rocky Hill, N.J.). A peptide library of a total of 103 15-mers with an overlap of 11 amino acids (AA) spanning CCNA1 (isoform c, NM_001111046) was purchased from Sigma (St. Louis, Mo.). Shorter peptides were purchased from Sigma or from JPT (Berlin, Germany).

Generation of CCNA1 Specific T Cell Clones.

T-cell lines were generated as described with minor modifications (Ho et al., 2006 *J Immunol Methods* 310

(1-2):40-52). Briefly, DCs were derived from the plastic adherent fraction of PBMCs by culture over two days (days −2 to 0) in DC media (CellGenix, Freiburg, Germany) supplemented with GM-CSF (800 U/ml) and IL-4 (1000 U/ml). On day −1, maturation cytokines TNFα (1100 U/ml), IL-1β (2000 U/ml), IL-6 (1000 U/ml) and PGE2 (1 µg/ml) were added. On day 0, DCs were harvested, washed and pulsed with peptide (single peptides at 10 µg/ml or peptide pools at 2 µg/ml) over 2 to 4 h in serum-free DC media. CD8 T cells were isolated from PBMCs using anti-CD8 microbeads (Miltenyi, Auburn, Calif.) and stimulated with DCs at an effector target (E:T) ratio of 1:5 to 1:10 in the presence of IL-21 (30 ng/ml). On day 3, IL-2 (12.5 U/ml), IL-7 (5 ng/ml) and IL-15 (5 ng/ml) were added. Cells were restimulated between days 10 and 14 using the plastic adherent faction of irradiated autologous PBMCs as antigen presenting cells (APCs) after being peptide-pulsed for two hours and in the presence of IL-21. After restimulation, cells were supplemented from day 1 on with IL-2 (25 U/ml), IL-7 (5 ng/ml) and IL-15 (5 ng/ml). T-cell clones were generated by plating cells at limiting dilution and expanding with TM-LCLs coated with OKT3™ muromonab-CD3 (OrthoBiotech, Bridgewater, N.J.) and allogeneic PBMCs as feeders (REP protocol) as described (Ho et al., 2006 *J Immunol Methods* 310 (1-2):40-52).

IFNγ Intracellular Staining (ICS).

APCs were pulsed with 10 µg/ml peptide overnight and washed once. Effector cells were coincubated with APCs for 6 h in RPMI containing 10% FBS in the presence of monensin. Cells were then stained with anti-CD8-FITC, permeabilized using the BD CYTOFIX/CYTOPERM™ cell staining kit, and stained with anti-IFNγ-allophycocyanin (all from BD Bioscience, Franklin Lakes, N.J.).

HLA Stabilization Assay.

T2 cells were pulsed with 100 µg/ml peptide in serum-free RPMI containing 1 µg/ml β-2-microglobulin (Sigma) for 16 h. Cells were then washed and incubated for 4 h in the presence of 5 µg/ml brefeldin A (Sigma), and then stained with FITC-labeled anti-HLA A, B, C (clone W6/32, BD Bioscience).

Caspase-3 Assay.

Target cells were membrane-labeled with PKH26 (Sigma) according to the manufacturer's instructions. T-cell clones were used at the end of the Rapid Expansion Protocol (REP, Riddell and Greenberg, 1990 *J Imm. Meth.* 128:189; Ho et al., 2006 *J. Imm. Meth.* 310:40) cycle (day 12 or later). Targets and T-cells were incubated at an E:T ratio of 3:1 in 96-well round-bottom plates at 37° C. for 4 h. As a negative control, targets were incubated without effectors, and, as a positive control, targets were incubated in the presence of 4 µM camptothecin (Sigma) or 1 µM staurosporine (Sigma). Cells were then fixed and permeabilized using the BD CYTOFIX/CYTOPERM™ cell staining kit according to the supplier's instructions, and stained with anti-active caspase-3 antibody conjugated either to FITC or Alexa-Fluor-647 (C92-625, BD Bioscience).

$^{51}$Chromium Release Assay.

A standard $^{51}$Cr release assay was performed as described (Ho et al., 2006 *J Immunol Methods* 310 (1-2):40-52) using 5000 target cells and T-cells at the end of the REP cycle (day 12 or later) at E:T ratios of 10-1.25:1 per well in triplicate. Spontaneous release was assessed by incubating targets in the absence of effectors. Percentage of specific lysis was calculated using the formula 100×(experimental release-spontaneous release)/(maximum release-spontaneous release).

Results

Selective Expression of CCNA1 in AML LSC, Leukemic Blasts and Testis.

To systematically screen for candidate target genes for T-cell mediated therapy that were selectively expressed in the AML LSC compartment with or without expression in other leukemic cell populations, nine LSC microarray data sets were analyzed along with samples of different hematopoietic cell subsets and non-hematopoietic tissues. Suitable candidate genes were identified by mathematical filtering and manual vetting of the model-based expression values. Based on the microarray data and published data on oncogenicity and cellular location of the respective genes, eight candidates including WT1 were identified, but only probe set 205899_at representing CCNA1 revealed selective expression in LSCs and AML blasts in the two independent microarray data sets and a third set of samples analyzed using qRT PCR.

In the first microarray set, CCNA1 was overexpressed in six out of nine analyzed LSC samples and testis. Expression values of CCNA1 were significantly higher in LSCs than in HSCs/CD34+ BM mononuclear cells, PBMCs, and a panel of tissue samples including testis (FIG. 1A). Statistical testing was performed on the array set actually used to select the target. Since no significant difference in CCNA1 expression was observed between the LSCs and leukemic blasts derived from the same patients (FIG. 1B), the expression pattern of CCNA1 was confirmed in additional sample sets not selected for LSCs. Parts of the second microarray data panel, in which CCNA1 was previously identified as being expressed at significantly higher levels in AML cells compared to BM CD34+ mononuclear cells, PBMCs, mobilized CD34+ cells and BM, have already been published (Stirewalt et al., 2008 *Genes Chromosomes Cancer* 47 (1):8-20). These AML data sets were now analyzed along with data sets of non-hematopoietic tissues and lymphatic organs including two specimens of testis tissue. Again, expression of CCNA1 was only detected in AML and testis, and its expression was significantly higher in AML than in the tissue samples from testis (p=0.0017).

Figure 2:
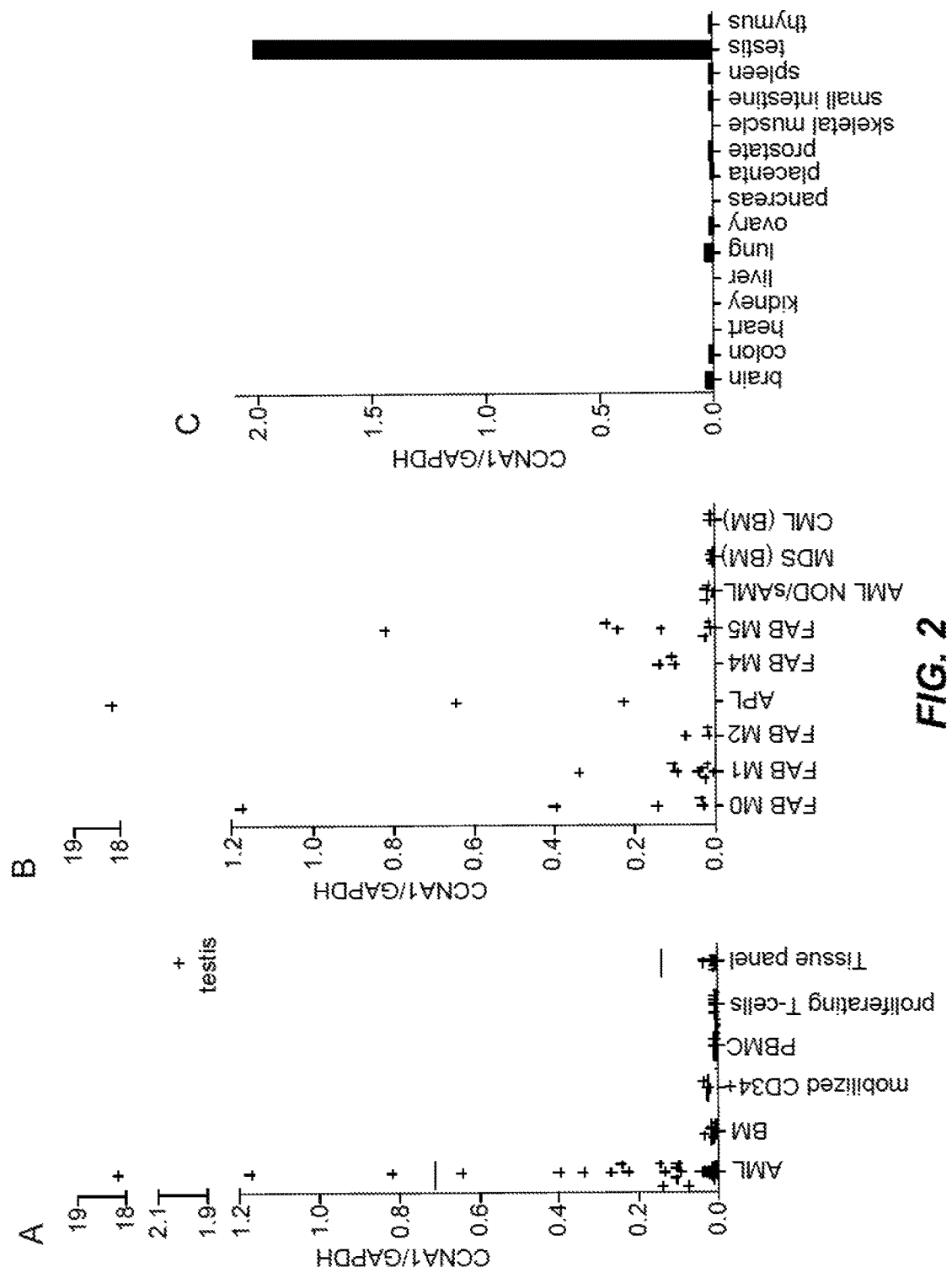
FIG. 2 shows CCNA1 expression quantified by qRT PCR: (A) in AML, healthy subsets of hematopoietic cells and tissues, (B) in AML FAB subtypes and BM of MDS and CML patients, (C) in healthy tissues.

To confirm the in silico findings and the validity of probe set 205899_at, CCNA1 was quantified in AML samples, in other hematopoietic cell subsets, and in a panel of non-hematopoietic tissues using qRT-PCR. Of 33 AML samples analyzed, 17 samples revealed expression of CCNA1 at levels at least twice as high as in every physiological sample measured except testis. No difference was observed between the CCNA1 expression levels in BM and G-CSF mobilized CD34+ mononuclear cells, which in both cases were very low. Lowest expression levels were found in maximally proliferating T-cells after OKT3 stimulation (FIG. 2A). Analyzing different French-American-British (FAB) AML subtypes and BM samples from patients with CML and MDS, variable percentages of aberrant CCNA1 expression were observed in AML, with the highest expression levels in acute promyelocytic leukemia (APL) and no overexpression in patients with secondary AML, MDS or CML (FIG. 2B). The median expression of CCNA1 copy numbers per GAPDH in the AML samples was approximately one order of magnitude higher than the expression of WT1 in the same sample set. In physiological tissues, CCNA1 was only expressed at detectable levels in testis (FIG. 2C).

Mapping of Multiple Immunogenic Oligopeptides on CCNA1.

For the identification of MHC class I-restricted T-cell epitopes, a reverse immunology approach was used. Four different CCNA1 mRNA variants have been described that code for three different isoforms, with isoform c distinguishable by having a shorter N-terminus. As no functional domains have been identified on the longer N-termini of isoforms a and b, and the respective transcripts for these isoforms could not be amplified by nested PCR, neither from testis nor AML samples, a peptide library representing only the shorter CCNA1 isoform c was used, so that immune escape due to targeting of epitopes in the N-termini could not occur as a consequence of cells switching CCNA1 isoforms and expressing only this shorter isoform.

After four stimulations of CD8 T-cells originating from HLA A*0201-positive donors 2196 and 2264 with the peptide library, more than 60% of cells in both T-cell lines appeared specific. Following (a) stimulation of T-cells with autologous LCL as APC pulsed with peptide pools, single 15-mers and subsequent shorter peptides, and (b) analysis of T-cell responses by intracellular staining for IFNγ, eight immunogenic oligopeptides were mapped. Donor 2196 CD8 T-cells identified immunogenic CCNA1 peptides that are identified here by the amino acid residue positions in the CCNA1 isoform c sequence:

```
                                        [SEQ ID NO: 1]
    CCNA1120-131 VDTGTLKSDLHF,

[SEQ ID NO: 2]
    CCNA1218-226 AETLYLAVN,

[SEQ ID NO: 3]
    CCNA1227-235 FLDRFLSCM,
    and
                                        [SEQ ID NO: 4]
    CCNA1253-261 ASKYEEIYP.
```

Donor 2264 CD8 T-cells identified the following immunogenic peptides from the CCNA1 isoform c polypeptide:

```
                                        [SEQ ID NO: 5]
    CCNA1118-127 YEVDTGTLKS,

[SEQ ID NO: 6]
    CCNA1167-175 YAEEIYQYL,

[SEQ ID NO: 7]
    CCNA1330-339 LEADPFLKYL,

[SEQ ID NO: 8]
    CCNA1341-351 SLIAAAAFCLA.
```

Using the two normal donors to assess potential T-cell responses to CCNA1 isoform c sequences, the eight immunogenic peptides stimulated T-cells in a manner characterized by MHC restriction against at least three different HLA class I molecules. CCNA1 was expressed strictly intracellularly and epitopes from it were processed and presented in the context of Class I MHC molecules. CCNA1 thus represented a suitable target for T-cell based therapy approaches.

T-cell clones were generated against the epitopes defined by the CCNA1 isoform c peptides 118-127 [SEQ ID NO:5], 227-235 [SEQ ID NO:3], 167-175 [SEQ ID NO:6], and 341-351 [SEQ ID NO:8]. Using 721.221 cells with and without stable transfected HLA A*0201 as APCs for T-cell lines in an IFNγ intracellular staining (ICS) assay, epitopes 218-226 [SEQ ID NO:2], 227-235 [SEQ ID NO:3], and 341-351 [SEQ ID NO:8] were found to be presented in a HLA A*0201-restricted manner. T-cell lines antigen-specifically directed against all three epitopes could be generated using cells from both donors.

Characterization of Two HLA A*0201 Restricted Epitopes.

Figure 3:
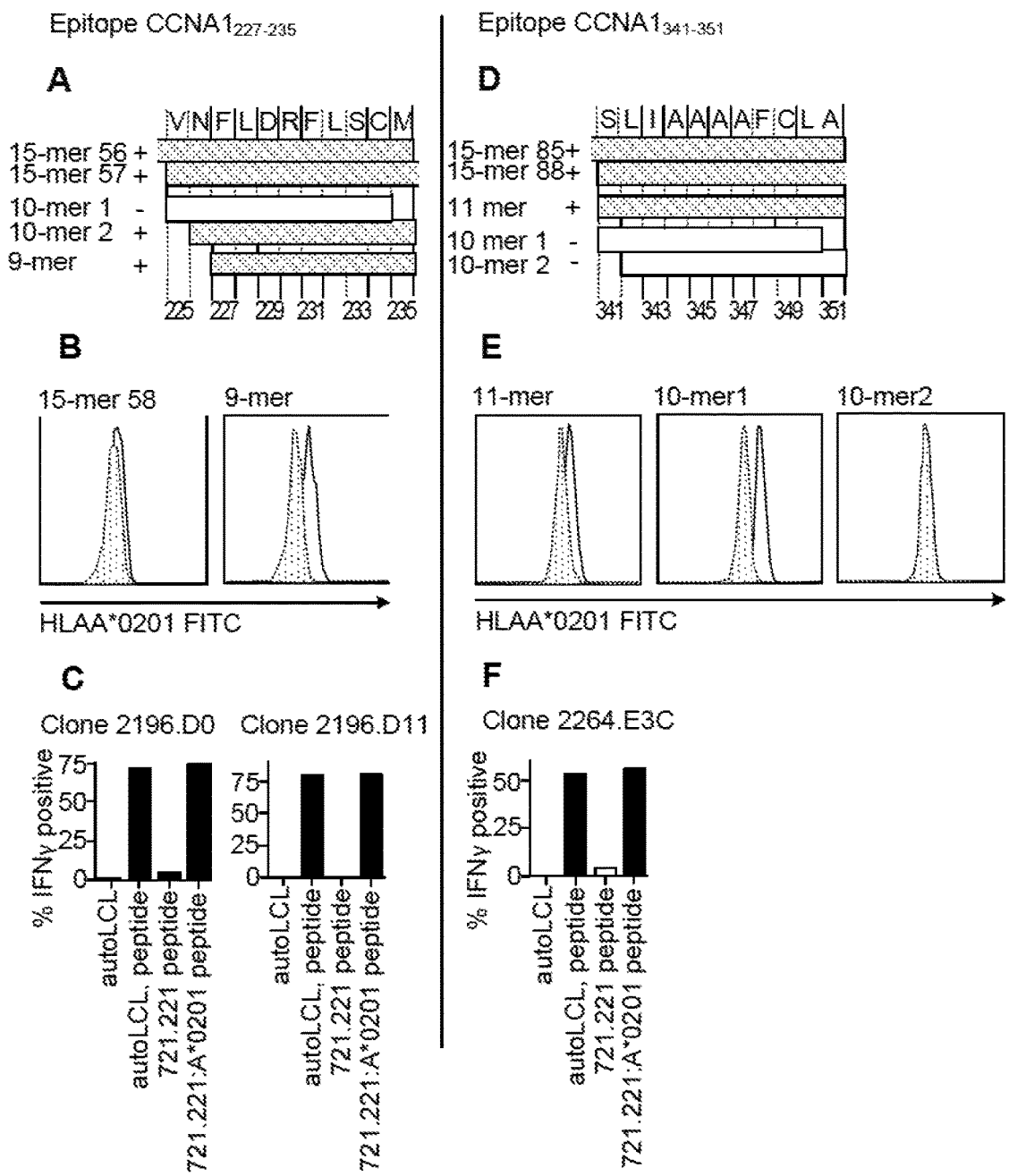
FIG. 3 shows HLA A*0201-restricted epitopes $CCNA1_{227-235}$ (A-C) and $CCNA1_{341-351}$ (D-F): (A, D) Mapping of the minimal immunogenic AA sequence using IFNγ intracellular staining (ICS). +/− refers to positivity of IFNγ after coincubation of the respective T-cell line with peptide pulsed autologous lymphoblastic cell lines (LCLs), (B, E) the immunogenic peptides stabilized HLA A*0201 on T2 cells. Negative controls were T2 cells pulsed with an irrelevant 15-mer (shaded), (C, F) activation of specific clones was dependent on peptide and expression of HLA A*0201. IFNγ ICS with autologous LCLs, 721.211 cells, and 721.221 stably transfected with HLA A*0201 as APCs.

The 9-mer FLDRFLSCM (CCNA1227-235, [SEQ ID NO:3]) was identified as the minimal immunogenic amino acid (AA) sequence from the library peptides 56/57 that stimulated a responses as revealed from analysis of a T-cell line from donor 2196 (FIG. 3A). The 9-mer enhanced the stabilization of HLA A*0201 on the T2 surface when compared to the 15-mer and an irrelevant 15-mer (FIG. 3 B). The IFNγ production of T-cell clones against this epitope was HLA A*0201 restricted (FIG. 3 C). The 11-mer SLIAAAAFCLA (CCNA1341-351, [SEQ ID NO:8]) was identified surprisingly as the minimal immunogenic AA sequence from library peptides 85/86, which stimulated a response in a T-cell line from donor 2264 (FIG. 3D). Even though the 10-mer SLIAAAAFCL (SEQ ID NO: 17) (10-mer 1) MHC complex was more stable than the complex with the 11-mer, only the latter was able to activate the analyzed T-cell clones (FIG. 3D, 3E). The IFNγ production of T-cell clones against this epitope was dependent on peptide 341-351 [SEQ ID NO:8] and HLA A*0201 expression (FIG. 3F).

Cytotoxic Activity of T-Cell Clones Specific for CCNA1 227-235 and CCNA1 341-351 Against the Leukemic Cell Line THP1.

Figure 4:
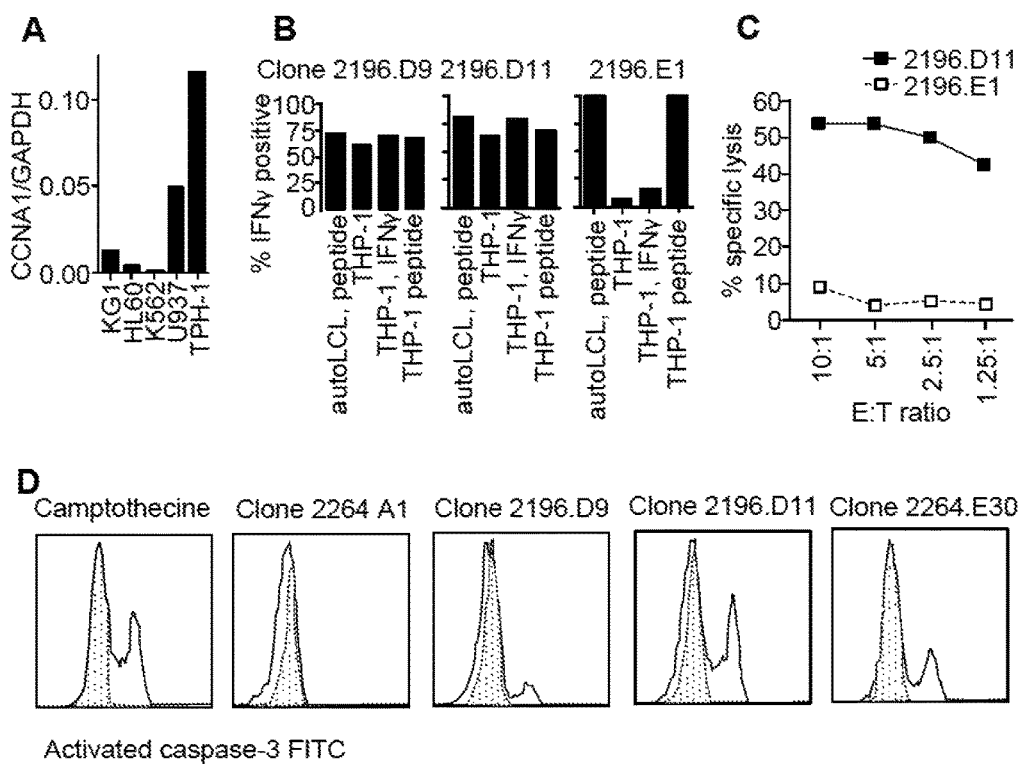
FIG. 4 shows T-cell clones against $CCNA1_{227-235}$ [SEQ ID NO:3] and $CCNA1_{341-351}$ [SEQ ID NO:8] displayed cytotoxic activity. (A) Expression of CCNA1 in several myeloid cell lines quantified by qRT PCR, (B) IFNγ ICS: high avidity clones 2196.D9 and D11 produced IFNγ in the presence of CCNA1+/HLA A*0201+ cell line THP-1 independent of exogenous peptide; low avidity clone 2196.E1 only recognized peptide-pulsed cell lines, (C) 6 h $^{51}$Cr release assay. Clone 2196.D11 caused specific lysis in THP-1. Low avidity clone 2196.E1 is shown for comparison, (D) Caspase-3 assay. Clones against both epitopes induced apoptosis in THP-1. Negative control: targets alone (shaded) and clone 2264.A1 specific for epitope CCNA1$_{118-127}$ [SEQ ID NO:5], which was HLA B*4001 restricted (data not shown, THP-1 was B*4001-negative), positive control: targets in presence of 4 μM camptothecine. 2196.D9, 2196.D11 were specific for epitope CCNA1$_{227-235}$ [SEQ ID NO:3], clone 2264.E30 was specific for epitope CCNA1$_{341-351}$ [SEQ ID NO:8].

To assess a suitable CCNA1 expressing leukemic cell line as a target cell, CCNA1 was quantified in five myeloid leukemia cell lines (FIG. 4A). THP-1, an HLA A*0201-positive FAB M5b AML line, was found to express the highest levels of CCNA1. Clones 2196.D9, 2196.D11 and 2196.E1, which were all specific for CCNA1 227-235 [SEQ ID NO:3], were tested for reactivity against THP-1. All three clones produced IFNγ after co-incubation with autologous LCLs that had been pulsed with the peptide epitope (FIG. 3C, 3F and data not shown), but only clones D9 and D11 displayed significant IFNγ production in response to THP-1. These responses were enhanced by incubating the THP-1 target cells with 1000 U/ml IFNγ for 16 h before coincubation with the effectors (FIG. 4B). Clone D11 showed significant lytic activity against THP-1 in a standard 6 h $^{51}$Cr release assay, while the low avidity clone E1 did not (FIG. 4C). Specific caspase-3 cleavage was observed not only for clones 2196.D9 and 2196.D11 but also for clone 2264.E30, which was directed against CCNA1341-351 [SEQ ID NO:8], indicating proper processing and presentation of both described HLA A*0201 epitopes (FIG. 4C, 4D).

Figure 6:
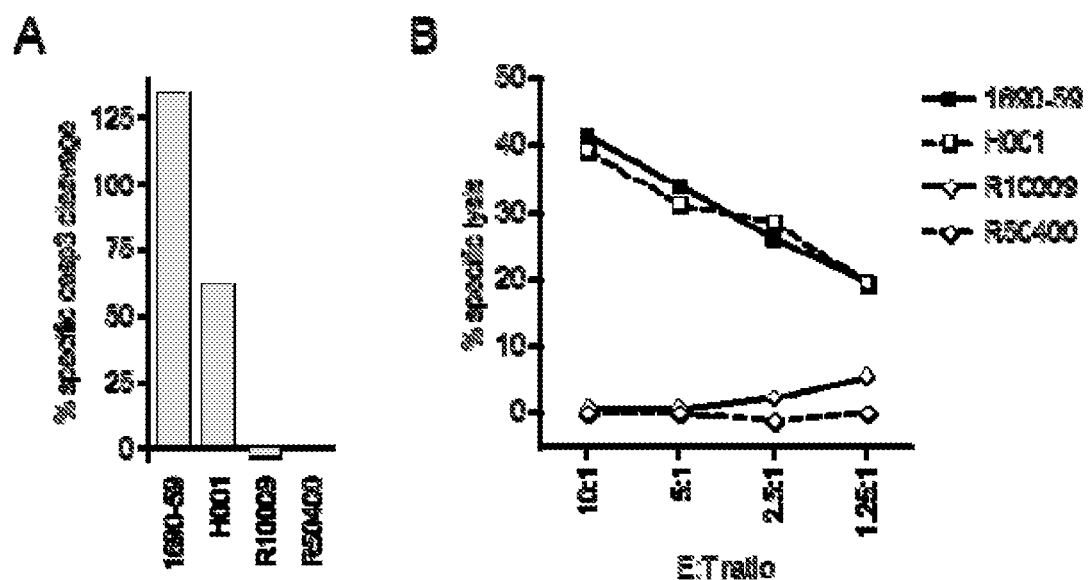
FIG. 6 shows activity of T-cell clone 2196.D11$_b$ specific for CCNA1$_{227-235}$ [SEQ ID NO:3] in an apoptosis induction (caspase-3) assay (FIG. 6A) and in a $^{51}$Cr release cytolysis assay (FIG. 6B).

Recognition and Lysis of Primary AML Cells by CD8+ T-cell clones specific for CCNA1 227-235. To determine if CTLs specific for a cyclin-A1 epitope recognized primary AML cells, cyclin-A1 expressing blasts from two A*0201-positive and two A*0201-negative patients were tested with clone 2196.D11$_b$, ("D11$_b$") which recognized epitope 227-235. 2196.D11$_b$ was first tested for induction of apoptosis in a four-hour caspase-3 assay. For maximal apoptosis of these targets, staurosporine was used. As the different AML samples showed different rates of spontaneous apoptosis, the data were normalized by calculating specific caspase-3 cleavage as 100×(experimental−spontaneous)/(staurosporine−spontaneous). Using an E:T ratio of 5:1, 2196.D11$_b$ induced significant apoptosis of the A*0201-positive AML specimens, but not A*0201-negative ones (FIG. 6A). To determine if the observed caspase-3 cleavage reflected classical lytic activity, a standard four-hour $^{51}$Cr release assay was performed over a range of E:T ratios. Significant lysis of the A*0201-positive specimens was observed at an E:T as low as 1.25:1, while no specific lysis was detectable in the A*0201-negative targets. Thus, primary AML cells were killed in an HLA-restricted fashion (FIG. 6B). H001 and 1690-59 were HLA A*0201 positive, and R10009 and R50400 were HLA A*0201-negative.

According to the criteria of the National Cancer Institute's list of weighted "ideal" cancer antigen criteria/characteristics (Cheever et al., 2009 Clin Cancer Res 15 (17):5323-5337), from the present disclosure CCNA1 appeared to be a highly suitable antigen for targeting AML because it was highly expressed in AML cells including the stem cell compartment of approximately 50% of patients, and the tissue distribution of CCNA1 expression was highly restricted. Both WT1 and CCNA1 were expressed at significantly higher levels in leukemia stem cells (LSCs) than in hematopoietic stem cells (HSGs) (Majeti et al., 2009 Proc Natl Acad Sci USA 106 (9): 3396-3401). However, unlike WT1, which was expressed in normal spleen, ovary and kidney at levels higher than in leukemic blasts, significant CCNA1 expression was found only in testis, which is generally considered an immune privileged site (Fijak et al., 2006 Immunol Rev 213:66-81. doi: IMR438 [pii] 10.1111/j.1600-065X.2006.00438.x). Consequently, cytotoxic side effects of targeting CCNA1 appear unlikely. CCNA1 has been reported to be oncogenic in mice, with overexpression resulting in the development of AML; CCNA1 expression sustained the malignant phenotype in AML (Chan et al., 2009 Oncogene 28 (43):3825-3836. doi: one 2009236 [pii] 10.1038/onc.2009.236; Jang et al., 2008 Cancer Res 68 (12):4559-4570. doi: 68/12/4559 [pii] 10.1158/0008-5472.CAN-08-0021; Ji et al., 2007 Int J Cancer 121 (4): 706-713. doi:10.1002/ijc. 22634).

Demonstration of specific in vitro cytotoxicity of T-cell clones generated against endogenously expressed and presented malignancy-associated self-antigens has been a subject of previous reports (Wilde et al., 2009 Blood 114 (10):2131-2139. doi: blood-2009-03-209387 [pii] 10.1182/blood-2009-03-209387; Doubrovina et al., 2004 Clin Cancer Res 10 (21):7207-7219. doi: 10/21/7207 [pii] 10.1158/1078-0432. CCR-04-1040; Chaise et al., 2008 Blood 112 (7):2956-2964. doi: blood-2008-02-137695 [pii] 10.1182/blood-2008-02-137695). Efficient cytotoxic activity of CCNA1-specific T-cell clones was observed against leukemia cells, as described herein. The level of CCNA1 expression appeared to be about one order of magnitude higher than that reported by others for WT1, the expression levels of which may oscillate as a function of the cell cycle. The CCNA1 protein is known to be regulated by the ubiquitin proteasome-mediated pathway (Ekberg et al., 2009 Mol Cell Biochem 320 (1-2):115-124. doi: 10.1007/s11010-008-9913-3), consistent with optimal presentation of its epitopes on the surface of malignant cells.

Due to its role in gametogenesis, and because it appears analogous to the published classification for cancer-testis-antigens, based on the present disclosure CCNA1 is hereby classified as a leukemia-testis-antigen of the non-X type (Simpson et al., 2005 Nat Rev Cancer 5 (8):615-625. doi: nrc1669 [pii] 10.1038/nrc1669). CCNA1 was expressed in LSCs and as disclosed herein appears to be the first described non-X leukemia-testis-antigen. The tissue-selective expression pattern of CCNA1, its high expression levels in AML, its function in oncogenesis, and the multitude of CCNA1 immunogenic T-cell epitopes described herein make CCNA1 an optimal target for T-cell based therapeutic approaches including those described herein, and also including vaccination and/or adoptive T-cell transfer.

Additional References: Yang et al., 2010 Cell Oncol 32 (1-2):131-143. doi: G7V87116 LNJ27 053 [pii] 10.3233/CLO-2009-0510; Brait et al., 2008 Cancer Epidemiol Biomarkers Prev 17 (10): 2786-2794. doi:17/10/2786 [pii] 10.1158/1055-9965. EPI-08-0192; Spisak et al., 2010 Dis Markers 28 (1):1-14. doi: K32K0082 1215536H [pii] 10.3233/DMA-2010-0677; Farhadieh et al., 2009 ANZ J Surg 79 (1-2):48-54. doi: ANS4799 [pii] 10.1111/j.1445-2197. 2008. 04799.x; Wegiel et al., 2008 J Natl Cancer Inst 100 (14):1022-1036. doi: djn214 [pii] 10.1093/jnci/djn214; Coletta et al., 2008 Cancer Res 68 (7):2204-2213. doi: 68/7/2204 [pii] 10.1158/0008-5472. CAN-07-3141; Cho et al., 2006 Cancer Sci 97 (10):1082-1092. doi: CAS292 [pii] 10.1111/j.1349-7006. 2006. 00292.x; Fijak et al., 2006 Immunol Rev 213:66-81. doi: IMR438 [pii] 10.1111/j.1600-065X.2006.00438.x; Rammensee et al., 1999 Immunogenetics 50 (3-4):213-219. doi:90500213.251 [pii]; Lundegaard et al., 2008 Nucleic Acids Res 36 (Web Server issue):W509-512. doi:gkn202 [pii] 10.1093/nar/gkn202.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

EQUIVALENTS

While particular steps, elements, embodiments and applications of the present invention have been shown and described herein for purposes of illustration, it will be understood, of course, that the invention is not limited thereto since modifications may be made by persons skilled in the art, particularly in light of the foregoing teachings, without deviating from the spirit and scope of the invention. Accordingly, the invention is not limited except as by the appended claims.

What is claimed is:

1. An isolated human cyclin A1 (CCNA1)-specific T cell comprising at least one recombinant expression vector encoding a T-cell receptor polypeptide that specifically binds in a human class I HLA-restricted manner to a CCNA1 polypeptide epitope of no more than 20, 19, 18, 17, 16, 15, 14, 13, 12, 11, 10, or 9 amino acids comprising the amino acid sequence set forth in SEQ ID NO:1, 3, 4, 5, 6, or 8.

2. A method for treating a condition characterized by CCNA1 overexpression in cells of a subject, comprising adoptively transferring to the subject an effective amount of the CCNA1-specific T cell of claim 1.

3. The isolated human CCNA1-specific T cell of claim 1 wherein the polypeptide epitope is a polypeptide of general formula:

N-X-C,    [I]

wherein:
(a) N-X-C is a polypeptide of no more than 20, 19, 18, 17, 16, 15, 14, 13, 12, 11, 10 or 9 amino acids in which X is an amino acid sequence that is selected from:

```
                                                      [SEQ ID NO: 1]
    CCNA1(120-131) VDTGTLKSDLHF,

[SEQ ID NO: 3]
    CCNA1(227-235) FLDRFLSCM,

[SEQ ID NO: 4]
    CCNA1(253-261) ASKYEEIYP,

[SEQ ID NO: 5]
    CCNA1(118-127) YEVDTGTLKS,

[SEQ ID NO: 6]
    CCNA1(167-175) YAEEIYQYL,
    and

[SEQ IN NO: 8]
    CCNA1(341-351) SLIAAAAFCLA,
```

(b) N is the amino terminus of the peptide and consists of 0, 1, 2, 3, 4, 5, 6, 7, 8, 9, 10 or 11 amino acids that are independently selected from natural amino acids and non-natural amino acids, and (c) C is the carboxy terminus of the peptide and consists of 0, 1, 2, 3, 4, 5, 6, 7, 8, 9, 10 or 11 amino acids that are independently selected from natural amino acids and non-natural amino acids.

* * * * *

SEQUENCE LISTING

<160> NUMBER OF SEQ ID NOS: 17

<210> SEQ ID NO 1
<211> LENGTH: 12
<212> TYPE: PRT
<213> ORGANISM: Artificial Sequence
<220> FEATURE:
<223> OTHER INFORMATION: Artificial Human Cyclin A1 Fragment

<400> SEQUENCE: 1

Val Asp Thr Gly Thr Leu Lys Ser Asp Leu His Phe
1               5                   10

<210> SEQ ID NO 2
<211> LENGTH: 9
<212> TYPE: PRT
<213> ORGANISM: Artificial Sequence
<220> FEATURE:
<223> OTHER INFORMATION: Artificial Human Cyclin A1 Fragment

<400> SEQUENCE: 2

Ala Glu Thr Leu Tyr Leu Ala Val Asn
1               5

<210> SEQ ID NO 3
<211> LENGTH: 9
<212> TYPE: PRT
<213> ORGANISM: Artificial Sequence
<220> FEATURE:
<223> OTHER INFORMATION: Artificial Human Cyclin A1 Fragment

<400> SEQUENCE: 3

Phe Leu Asp Arg Phe Leu Ser Cys Met
1               5

<210> SEQ ID NO 4
<211> LENGTH: 9
<212> TYPE: PRT
<213> ORGANISM: Artificial Sequence
<220> FEATURE:
<223> OTHER INFORMATION: Artificial Human Cyclin A1 Fragment

<400> SEQUENCE: 4

Ala Ser Lys Tyr Glu Glu Ile Tyr Pro
1               5

<210> SEQ ID NO 5
<211> LENGTH: 10
<212> TYPE: PRT
<213> ORGANISM: Artificial Sequence
<220> FEATURE:
<223> OTHER INFORMATION: Artificial Human Cyclin A1 Fragment

<400> SEQUENCE: 5

Tyr Glu Val Asp Thr Gly Thr Leu Lys Ser
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Artificial Human Cyclin A1 Fragment

<400> SEQUENCE: 6

Tyr Ala Glu Glu Ile Tyr Gln Tyr Leu
1               5

<210> SEQ ID NO 7
<211> LENGTH: 10
<212> TYPE: PRT
<213> ORGANISM: Artificial Sequence
<220> FEATURE:

<223> OTHER INFORMATION: Artificial Human Cyclin A1 Fragment

<400> SEQUENCE: 7

Leu Glu Ala Asp Pro Phe Leu Lys Tyr Leu
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Artificial Human Cyclin A1 Fragment

<400> SEQUENCE: 8

Ser Leu Ile Ala Ala Ala Ala Phe Cys Leu Ala
1               5                   10

<210> SEQ ID NO 9
<211> LENGTH: 421
<212> TYPE: PRT
<213> ORGANISM: Homo Sapiens
<300> PUBLICATION INFORMATION:
<308> DATABASE ACCESSION NUMBER: NCBI / NP_001104517.1 GI:611377472
<309> DATABASE ENTRY DATE: 2007-11-30
<313> RELEVANT RESIDUES IN SEQ ID NO: (1)..(421)

<400> SEQUENCE: 9

Met His Cys Ser Asn Pro Lys Ser Gly Val Val Leu Ala Thr Val Ala
1               5                   10                  15

Arg Gly Pro Asp Ala Cys Gln Ile Leu Thr Arg Ala Pro Leu Gly Gln
                20                  25                  30

Asp Pro Pro Gln Arg Thr Val Leu Gly Leu Leu Thr Ala Asn Gly Gln
            35                  40                  45

Tyr Arg Arg Thr Cys Gly Gln Gly Ile Thr Arg Ile Arg Cys Tyr Ser
        50                  55                  60

Gly Ser Glu Asn Ala Phe Pro Pro Ala Gly Lys Lys Ala Leu Pro Asp
65                  70                  75                  80

Cys Gly Val Gln Glu Pro Pro Lys Gln Gly Phe Asp Ile Tyr Met Asp
                85                  90                  95

Glu Leu Glu Gln Gly Asp Arg Asp Ser Cys Ser Val Arg Glu Gly Met
            100                 105                 110

Ala Phe Glu Asp Val Tyr Glu Val Asp Thr Gly Thr Leu Lys Ser Asp
        115                 120                 125

Leu His Phe Leu Leu Asp Phe Asn Thr Val Ser Pro Met Leu Val Asp
    130                 135                 140

Ser Ser Leu Leu Ser Gln Ser Glu Asp Ile Ser Ser Leu Gly Thr Asp
145                 150                 155                 160

Val Ile Asn Val Thr Glu Tyr Ala Glu Glu Ile Tyr Gln Tyr Leu Arg
                165                 170                 175

Glu Ala Glu Ile Arg His Arg Pro Lys Ala His Tyr Met Lys Lys Gln
            180                 185                 190

Pro Asp Ile Thr Glu Gly Met Arg Thr Ile Leu Val Asp Trp Leu Val
        195                 200                 205

Glu Val Gly Glu Glu Tyr Lys Leu Arg Ala Glu Thr Leu Tyr Leu Ala
    210                 215                 220

Val Asn Phe Leu Asp Arg Phe Leu Ser Cys Met Ser Val Leu Arg Gly
225                 230                 235                 240

Lys Leu Gln Leu Val Gly Thr Ala Ala Met Leu Leu Ala Ser Lys Tyr
                245                 250                 255

```
Glu Ile Tyr Pro Pro Val Asp Glu Phe Val Tyr Ile Thr Asp
    260             265             270
Asp Thr Tyr Thr Lys Arg Gln Leu Leu Lys Met Glu His Leu Leu Leu
        275                 280                 285
Lys Val Leu Ala Phe Asp Leu Thr Val Pro Thr Thr Asn Gln Phe Leu
    290                 295                 300
Leu Gln Tyr Leu Arg Arg Gln Gly Val Cys Val Arg Thr Glu Asn Leu
305                 310                 315                 320
Ala Lys Tyr Val Ala Glu Leu Ser Leu Leu Glu Ala Asp Pro Phe Leu
            325                 330                 335
Lys Tyr Leu Pro Ser Leu Ile Ala Ala Ala Phe Cys Leu Ala Asn
            340                 345             350
Tyr Thr Val Asn Lys His Phe Trp Pro Glu Thr Leu Ala Ala Phe Thr
            355                 360                 365
Gly Tyr Ser Leu Ser Glu Ile Val Pro Cys Leu Ser Glu Leu His Lys
    370                 375                 380
Ala Tyr Leu Asp Ile Pro His Arg Pro Gln Gln Ala Ile Arg Glu Lys
385                 390                 395                 400
Tyr Lys Ala Ser Lys Tyr Leu Cys Val Ser Leu Met Glu Pro Pro Ala
                405                 410                 415
Val Leu Leu Leu Gln
            420

<210> SEQ ID NO 10
<211> LENGTH: 1841
<212> TYPE: DNA
<213> ORGANISM: Homo Sapiens
<300> PUBLICATION INFORMATION:
<308> DATABASE ACCESSION NUMBER: NCBI / NM001111047.1 GI161377471
<309> DATABASE ENTRY DATE: 2007-11-30
<313> RELEVANT RESIDUES IN SEQ ID NO: (1)..(1841)

<400> SEQUENCE: 10
gccgcagcct gcgcagcccc gaggaccccg cgtcgctctc ccgagccagg gttctcagga      60 gcggccgcg caggagacgt tagaggggggt tgttagcggc tgttgggaga acgggtcacg     120
gaaacagtcc cttccaaagc cggggccatc gtggggtggg cgagtccgcc ctcccaggcc     180
gggggcgcgg accagagggg acgtgtgcag acggccgcgg tcagccccac ctcgcccggg     240
cggagacgca cagctggagc tggagggccg tcgcccgttg ggccctcagg ggcctgaacg     300
cccaggggtc gcggcgagtc caccccggagc gagtcagcag cccgtggagt ctgaagcaat     360
gcactgcagc aaccccaaga gtggagttgt gctggctaca gtggcccgag gtcccgatgc     420
ttgtcagata ctcaccagag ccccgctggg ccaggatccc ccgcagagga cagtgctagg     480
gctgctaact gcaaatgggc agtacaggag gacctgtggc caggggatca aagaatcag     540 gtgttattct ggatcagaaa atgccttccc tccagctgga agaaagcac tccctgactg     600 tggggtccaa gagcccccca gcaagggtt tgacatctac atggatgaac tagagcaggg     660
ggacagagac agctgctcgg tcagagaggg gatggcattt gaggatgtgt atgaagtaga     720
caccggcaca ctcaagtcag acctgcactt cctgctggat ttcaacacag ttttcccctat     780 gctggtagat tcatctctcc tctcccagtc tgaagatata tccagtcttg cacagatgt     840 gataaatgtg actgaatatg ctgaagaaat ttatcagtac cttagggaag ctgaataag     900 gcacagaccc aaagcacact acatgaagaa cagccagac atcacggaag gcatgcgcac     960
gattctggtg gactggctgg tggaggttgg ggaagaatat aaacttcgag cagagaccct    1020
```

-continued

```
gtatctggct gtcaacttcc tggacaggtt cctttcatgt atgtctgttc tgagagggaa    1080
actgcagctc gtaggaacag cagctatgct tttggcttcg aaatatgaag agatatatcc    1140
tcctgaagta gacgagtttg tctatatcac cgatgataca tacacaaaac gacaactgtt    1200
aaaaatggaa cacttgcttc tgaaagttct agcttttgat ctgacagtac caaccaccaa    1260
ccagtttctc cttcagtact tgaggcgaca aggagtgtgc gtcaggactg agaacctggc    1320
taagtacgta gcagagctga gtctacttga agcagatcca ttcttgaaat atcttccttc    1380
actgatagct gcagcagctt tttgcctggc aaactatact gtgaacaagc acttttggcc    1440 agaaacccctt gctgcattta cagggtattc attaagtgaa attgtgcctt gcctgagtga    1500
gcttcataaa gcgtaccttg atataccccca tcgacctcag caagcaatta gggagaagta    1560
caaggcttca agtacctgt gtgtgtccct catgggagcca cctgcagttc ttcttctaca    1620
ataagtttct gaatggaagc acttccagaa cttcacctcc atatcagaag tgccaataat    1680
cgtcataggc ttctgcacgt tggatcaact aatgttgttt acaatataga tgacatttta    1740
aaaatgtaaa tgaatttagt ttcccttaga ctttagtagt ttgtaatata gtccaacatt    1800
ttttaaacaa taaactgctt gtcttatgac catgtgttag a                        1841
```

<210> SEQ ID NO 11
<211> LENGTH: 20
<212> TYPE: DNA
<213> ORGANISM: Artificial Sequence
<220> FEATURE:
<223> OTHER INFORMATION: GAPDH_fwd

<400> SEQUENCE: 11
gagtcaacgg atttggtcgt                                                20

<210> SEQ ID NO 12
<211> LENGTH: 25
<212> TYPE: DNA
<213> ORGANISM: Artificial Sequence
<220> FEATURE:
<223> OTHER INFORMATION: GAPDH_probe

<400> SEQUENCE: 12
gatattgttg ccatcaatga ccccct                                         25

<210> SEQ ID NO 13
<211> LENGTH: 20
<212> TYPE: DNA
<213> ORGANISM: Artificial Sequence
<220> FEATURE:
<223> OTHER INFORMATION: GAPDH_rev

<400> SEQUENCE: 13
gacaagcttc ccgttctcag                                                20

<210> SEQ ID NO 14
<211> LENGTH: 20
<212> TYPE: DNA
<213> ORGANISM: Artificial Sequence
<220> FEATURE:
<223> OTHER INFORMATION: CCNA1_fwd

<400> SEQUENCE: 14
catgaagaag cagccagaca                                                20

<210> SEQ ID NO 15

```
<211> LENGTH: 24
<212> TYPE: DNA
<213> ORGANISM: Artificial Sequence
<220> FEATURE:
<223> OTHER INFORMATION: CCNA1_probe

<400> SEQUENCE: 15
ttcgagcaga gaccctgtat ctgg                                            24

<210> SEQ ID NO 16
<211> LENGTH: 20
<212> TYPE: DNA
<213> ORGANISM: Artificial Sequence
<220> FEATURE:
<223> OTHER INFORMATION: CCNA1_rev

<400> SEQUENCE: 16
ttcgaagcca aaagcatagc                                                 20

<210> SEQ ID NO 17
<211> LENGTH: 10
<212> TYPE: PRT
<213> ORGANISM: Artificial Sequence
<220> FEATURE:
<223> OTHER INFORMATION: Artificial Human Cyclin A1 Fragment

<400> SEQUENCE: 17

Ser Leu Ile Ala Ala Ala Ala Phe Cys Leu
1               5                   10
```